(12) United States Patent
Berg et al.

(10) Patent No.: US 6,197,507 B1
(45) Date of Patent: Mar. 6, 2001

(54) GENETIC TEST FOR α-MANNOSIDOSIS

(76) Inventors: Thomas Berg; Ole Kristien Tollersrud; Oivind Nilssen, all of Institute of Clinical Medicine, Dept. of Medical Genetics, University of Tromso, N-9037, Tromso (NO)

( * ) Notice: Subject to any disclaimer, the term of this patent is extended or adjusted under 35 U.S.C. 154(b) by 0 days.

(21) Appl. No.: 09/101,886

(22) PCT Filed: Jan. 15, 1997

(86) PCT No.: PCT/GB97/00109

§ 371 Date: Jan. 29, 1999

§ 102(e) Date: Jan. 29, 1999

(87) PCT Pub. No.: WO97/26369

PCT Pub. Date: Jul. 24, 1997

(30) Foreign Application Priority Data

Jan. 15, 1996 (NO) ......................................... 960163

(51) Int. Cl.[7] .............................. C12Q 1/68; C12Q 1/48; C12Q 1/44; C12P 19/34; C07H 21/04
(52) U.S. Cl. .................................. 435/6; 435/15; 435/19; 435/91.2; 536/23.2; 536/23.5; 536/24.31; 536/24.33
(58) Field of Search ................................. 435/6, 15, 19, 435/91.2; 536/23.2, 23.5, 24.31, 24.33

(56) References Cited

PUBLICATIONS

Healy, P.J. et al. Australian Veterinary Journal 72(10):392, Oct. 1995.*
Tollersrud, O. K. et al. Accession No. L31373, Dec. 1995.*
Nebes, V.L. et al. Biochem. Biophys. Res. Comm. 200(1):239–45, Apr. 1994.*
Nebes, V.L. et al. Biochem. Biophys. Res. Comm. 232(2):583 (ERRATUM), Mar. 1997.*
Nebes, V.L. et al. Accession No. U05572, Jul. 1996.*
Liao, Y–F. et al. J. Biol. Chem. 271(45):28348–28358, Nov. 1996.*
Liao, Y–F. et al. Accession No. U68567, Nov. 1996.*
Nilssen, O. et al. Am. J. Human Gen. 57(4) Suppl:A39, Oct. 1995.*
Wang, W. et al. Am. J. Human Gen. 59(4) Suppl:A403, Oct. 1996.*
Gotoda, Y. et al. Am. J. Human Gen. 59(4) Suppl:A260, Oct. 1996.*
Tollersrud, O.K. et al. Eur. J. Biochem. 246:410–419, Jun. 1997.*
Berg, T. et al. Res. Vet. Science 63(3):279–82, Nov. 1997.*
H.W. Leipold et al., *JAVMA*, vol. 175, No. 5, (1979), pp. 457–459.
D.H. Embury et al., *Vet. Pathol.*, vol. 22, (1985), pp. 548–551.
J. Schatzle et al., *Journal of Biological Chemistry*, vol. 267, No. 6, (1992), pp. 4000–4007.
Healy et al., *Research in Veterinary Science*, vol. 49 (1990), pp. 82–84.
Chester, et al., 1982, in *Genetic Errors of Glycoprotein Metabolism*, pp. 90–122, Springer Verlag, Berlin.
Healy et al., *Research in Veterinary Science*, vol. 30, 1981, pp. 281–283.
Tollersrud et al., 1995, 10th ESGLD Workshop, Cambridge, England (vol./pages not available).
C. Emiliani et al., *Biochem. J.*, vol. 305, (1995), pp. 363–366.

* cited by examiner

Primary Examiner—Carla J. Myers
Assistant Examiner—Diana Johannsen
(74) Attorney, Agent, or Firm—Rothwell, Figg, Ernst & Manbeck

(57) ABSTRACT

A method for diagnosing or screening for bovine α-mannosidosis comprises detecting in nucleic acid samples from cattle the presence or absence of α-mannosidosis-causing mutations in the gene encoding bovine lysosomal α-mannosidase (LAMAN). A method of detecting α-mannosidosis-causing mutations in cattle comprises detecting the presence or absence of base transitions in the gene encoding bovine LAMAN which are associated with the disease.

16 Claims, 15 Drawing Sheets

FIG. 1

```
                                                                                +74
     GCGGCTGAGAGCCATGGTTGGTGACGGCGCCCTTCAGGGGTTGCGCTGCGGGGCCGGTAGGATCCCGGACGAGCTC
                M  V  G  D  A  R  P  S  G  V  R  A  G  G  C  R  G  A  V  G  S  R  T  S  S
(1-25)
     CCGCGGCGCTGGCCACGGCTCCGCGCCTCTCCCCTCGTGTTCCTGTTCCTAGCGGCGCCCTGCGTTGGGCGGGGATACAAG
                                                                                +250
         R  A  L  R  P  P  L  P  S  L  F  V  L  F  L  A  A  P  C  A  W  A  A  G  Y  K
(55-83)
     ACATGCCCGAAGGTGAAGCCGACATGCTGAATACACCGGTCGTCACACACATGATGATGTAGGCTCCTGCTGTGACC
         T  C  P  K  V  K  P  D  M  L  N  V  H  L  V  P  H  T  H  D  D  V  G  W  L  K  T  V  D
(114-142)
     AGTACTTCTATGGCATCTACAATAACATCCAGCCGGCGGTGTACAGTACATCGTCAGTCTCTTGCTGCGAATCC
                                                                                +426
         Q  Y  F  Y  G  I  Y  N  N  I  Q  P  A  G  V  Q  Y  I  L  D  S  V  I  S  S  L  A  N  P
     CACCCGCCGCTTCATCTATGTGGAAATCGCCTTCTTCCGGTGGGTCGCCAGAGACAATGCAACACAGAAATCGTGAGGGAA
         T  R  F  I  Y  V  E  I  A  F  F  S  R  W  R  Q  Q  T  Ⓝ A  T  Q  K  I  V  R  E
(172-201)
     CTGGTGGCCAGGGACGGCCTTCGCCAACGGTGCTGGGTGATGAACGATGAGGCCACCACTACGGAGCCATCATTGACC
                                                                                +602
         L  V  R  Q  G  R  L  E  F  A  N  G  G  W  V  M  N  D  E  A  T  T  H  Y  G  A  I  I  D
     AGATGACACTCAGACTGCGCTTCACTGTTCGCCAGATGGGTTTGACGGCCTCTCTTTGGACGGCGTCCTGATTATCAAGACAAGAAGTGCGG
         Q  M  L  R  L  T  R  F  L  E  E  T  F  G  S  D  G  R  P  R  V  A  W  H  I  D  P  F  G  H
(231-259)
     CTCGGGAGCAAGCTTCACTGTTCGCCAGATGGGTTTGACGGCCTCTCTTTGGACGGCGTCCTGATTATCAAGACAAGAAGTGCGG
                                                                                +778
         S  R  E  Q  A  S  L  F  A  Q  M  G  F  D  G  F  F  F  G  R  L  D  Y  Q  D  K  K  V  R
     AAAAGAGCTGCAGATGAGCAGGTGTGGCGGGCCAGCCTGAAACCTCCAACTGCCCTTCACCAGTGTGCTCCCCA
         K  K  T  L  Q  M  E  Q  V  W  R  A  S  T  S  L  K  P  P  T  A  D  L  F  T  S  V  L  P
(290-318)
     ACATGTACAACCCGCCCGAAGGTCTGTGCTGGGACATGCTGTGTGCCGACAAGCCGGTTGTGGAGGACACGCGTAGCCCAGAGTACAA
                                                                                +954
         N  M  Y  N  P  P  E  G  L  C  W  D  M  L  C  A  D  K  P  V  V  E  D  T  R  S  P  E  Y  N
     CGCAAAGAGAGCTGTGTCCGTAAGCTCCTGAAGTTGGCCACTGACCAGGGTAAGCTCGTCATCAGTGTTCAATCTTGACAAGCGGCAACG
         A  K  E  L  V  R  Y  F  L  K  L  A  T  D  Q  G  K  L  Y  R  T  K  H  T  V  M  T  M  G
(348-377)
     TCAGACTTCCAGTACGAGAATGCCAACTGGTTCAAAAATCTTGACAAGCTGAGCTGGGAGCTGGAACAACTTGCAGCAAAATTGGAAAAGGA
                                                                                +1130
         S  D  F  Q  Y  E  N  A  N  T  W  F  K  N  L  D  K  L  I  Q  L  V  N  A  Q  Q  R  A  N
     GGATCCGGTCAATGTTCTCTACGGCTCGAGCTGCTACCTGTGGAACTGTTCTGAACGCGGTTACTGTTCTGAACTGTTTCCAGCCGCTCTC
         G  I  R  V  N  V  L  Y  S  T  S  A  C  Y  L  W  E  L  N  K  A  Ⓝ L  S  W  S  V  K  K  D
(407-435)
     TGACTTCTCTCCCCTATGCTGAATGGCCCAGCTCTACATGTTCTGAACGCGGTTACTGTTCTTCCGGCAGCCAGTGGGACAGTG
         D  F  F  P  Y  A  D  G  P  Y  M  F  W  T  G  Y  F  S  S  R  P  A  L  K  R  Y  E  R  L
     AGCTACAATTTCCTGCAGGTGTGCAACAGCCGGGGATGTGCCTCCAGCAGCAGATGATCAGTGGACAGCATGCCCGG
                                                                                +1306
         S  Y  N  F  L  Q  V  C  N  Q  L  E  A  L  A  G  P  A  A  N  V  G  P  Y  G  S  G  D  S
     CACCCCTCAATGAGGCGATGGCCGTGCTCCAGCACGATGCAGTGAGTGGCACTTCAGCCGCCATCATGGCTTAAAGGCTTAAGGGCTTATGCCCG
         A  P  L  N  E  A  M  A  V  L  Q  H  H  D  A  V  S  G  T  S  R  Q  H  V  A  N  D  Y  A  R
(466-494)
     CCAACTTTCAGAAGGCTGAAGCTGGGAGTGGAGGCCCTGAAGTTCTCAGCATTTGTCCTGAGCAGCAGAGAGAATTCCAGTTGATCGTTTATACAAAG
                                                                                +1482
         Q  L  S  E  G  W  R  P  C  E  V  L  M  S  N  A  L  A  H  L  S  G  L  K  E  D  F  A  F
     TGTCGCAAGCTCAACATCAGCATTTGTCCTGAGCAGCAGAGAGAATTCCAGTTGATCGTTTATACAAAG
```

```
GCGGCTGCGAGAGCCATGGTTGGTGACGCGCGGGCCTTCAGGGGTTCGCGGTTGCCGGGGCGCTGCCGGGGCGGTAGGATCCCG
GACGAGCTCCCGCGCTGCGGCTGCGCCACCGCTCCCGCTCTCTCCTCCCTCTTCGTGTTGTTCCTAGCGCGCCCTGCGCT
TGGGCGGCGGGATACAAGtgagcgcgg cccgctagcg gaaatgtaca agagccatag tgaagcctcc
agtagagtcg gaggtgtgtg cgtgggtctg tttgtgggt gcccagtgaa tggttgctaa tatgacagtg
tgatctggtt catgctttgt gttactgaga agactggctg tgttagtctg agaatggggc tgtctgtgtc
tgtctcttgc ttctgtggat tggcttacct ggacttggca agcatttaca cgagcgggct gtgtggtggg
gactggttga gagttgggag tcagctgcct gaagtttaa cctgacttct caacttgtga ccttggccaa
atcacntcac ttctctgagc ctctgtattc tcatctgaaa actggagata atgttgccct caggtcccag
ggtgcctgct tggtattaac aaatgcttaa taaacatgag ctactactag tgttccga gggcatgaac
gagaggtgct ctgagaagtt ctgtcagttg gggagtacat ctatgacaca actatgtgtg tccttcttag
gggagccgat cccacctgt cacttgcttc tagatcaaga cttaccttat atcctcccaa cccncactg
cagcctgcct cttaaccttg gagttactga cagagtgagt gtgtgtttgg ggtcctgtg
cagACATGCCCGAAGGTGACCAGTACTTCTATGGCA gtgagtagag gagggtgggg agtgacccct gggactccca
AGACGGTGGACCAGTCCTGAAGCCGGACATGCTGAATGCTGTGCCTCACACACATGATGATGTAGGCTGGCTCA
tggtcctgcg gagcccttaa aattcctttt caggcctgga caatcagggt ggggcaaca cccagcttgg
gctcctgtgt ctaagaatgt ttcccttggc ttgctgattt ctgattgnct gaccccctgtg cccacag
TCTACAATAACATCTATGTGGAAATCGCCTTCTTTCTTCGCGTTGTACAGTAGTACATCCTAGACTCCGTCATCTCTTCCTTGCTGGCGAATCCCACCG
CCGCTTCATCTATGTGGAAATCGCCTTCTCTTCGCGTTGTGGCGCCAGCACACAAATGCAACACAGAAAATCGTGAGG
GAACTGGTGCGCAGG gtgagcctcc cttcaggaag tgaaaagagg aagccaagccagcttctat
ctctagcacc ctggcttctg agatttttat acgccatttg cagcctctat gtggctgccg ttgctgcttc
tgctaagtcg cttcaatcgt gtccgactct gtgtgaccc atagacagca gcccagcaga ctcccccatc
cctgggattc tccaggcaag aacactggag tggattgtgt tccatagctc tcttacactg gctgagagt
gaccctgac ccttctctc tcaggcctgg tcgtttaagc agtcttctc gtccctggca tcaccaacc
tggcgccactcctggcctgcgacaactgactgcctccgcacagGACGCGCCTAGAGTTCGCCAACGGTGG
CTGGGTGATGAACGATGAGGCGACCACCACCGACCCCCGTGCCCTGGCACATCGACCCATTCGACCACTCTCGGAGCAAGCTTCAC
GAGACGTTCGGCAGCGACGGGCGCCCCCGTGCCCTGGCACATCGACCCATTCGACCACTCTCGGAGCAAGCTTCAC
TGTTCGCGCAG tggctgggtg atgaacgatg aggcagcgac ccactacgga gccatcatcg accagatgac
actcagactg cgcttcctgg aggagacgtt cggcagcgac gggcgcccc gtgtggcctg gcacatcgac
ccattccgcc actctcggga gcaagcttca ctgttcgcgc agttttcag atctcttggg ccgccctt
cattccttct gactcctcct ctgtcatcca agccccgccc ttttctgnaa gt tcacccgaac ccgaaccagg
```

FIG. 2 CONT'D

```
ccctacccct ggncctctcg ccacttaaga ccctgcctct tgggtgacct gtgaatccca ttctttngg
tctggccttg gttctgtctct gtcctagnct aggttgacct catcaactat tcccatacaa cccgnctcc
cttgtcaggt gagtntcccc ctccctgatc canccagttg gtctgatctg gtnttggcaa gtggtggttg
tagggctggg tttcancagt tcgtactgtgcatacaccct cctgtagtng ganggagcnc tgatggagng
gtgtgggtgg tgtcccggtt cnaggtntac tccaaa *   canctttcnt gnctgcctcc ttccaaccgg
gtnacctaaa caatccaaaa cccggcncct tgcaatnatc tcccctccct gatcaacaag ttntctgacc
tgctcttgcc caacctggtg gctggttagg ncctcggttt ttcaaccaac ctcgttacct gtnccatgac
catcccccct cccttgctag gctgcggaaa gggaaggcc tcctaganct gggaaggtg gaggtgggtt
gtagcgttgg acttgctccc tccggcgct tccgcaggge ttctgacctt cctcagcctt tgaaatgaac
tggagggcct cgctgtctt tgacntggtt tttctccctg tgcgtgagag gttggtggtt ggtgatgaga
ggaccggtcc cttatgcatc ctgccctctc ntgntctccc anccactcg tcatccctcc ccanctccag
ATGGGTTTTGACGGCTTCTCTTTGGACGCCTGGATTATCAAGACAAGAAG GTGCGGAAAA
AGACGCTGCAGATGGAGCAGGTGTGGCGGGCCAGCAGCCTGAAACCTCCCACTGCCGAC CTCTTCACCA
gtaaggtggt agagtggaaa gaggg/ccgcc cccgtgctca gaaggcct gggcttggtt tatgtctgc
tatcattgtc ttgaaattcc tagtagttta tgaacagggg cccaccattt gc/gagtttgca ctgggcctgg
caaattctga aatccatccc cggtgaggcc tggc/taggtc tagggccatg accacccct gaacctaatg
tggtccgcag GTGTGCTCCCC AACATGTACAACCCGCCGG
AAGGTCTGTGCTGGGACATGCTGTGTGCCGACAAGCCGGTTGTGCCGAGGACACGCGTAGCCCAGAGTACAACGCAAAAGA
GCTGGTCC GTTACTTCCTGAAGTTGGCCACTGACCAG gtaaccgggt gtccagaacc tatgcctcca
gtgtacacgc actgggccct tccatcggcc cagacaatcc ctagcactc ctcaccttca ctgggggaag
gtaaaattcc attcaccatc accataccct gctcctggat ttgtgtgcat ttctgattag aaaggtggag
cccttcgcca gagcacatcc ccaccatgt tgntagacag catgnacag gacctcagta cccatgtctg
ggtggtaggc ccaagagaat tcctcaaccg cttgtggctc ttttctgtg tgtccctctg ctcccatgtg
acacacttcc accctaccc cccatggctc tgtgcactca cattcttttt atttaaaaaa ataattt *
ttgtttttgc ctgtactggg tccttttgttn cnaatccgna caatttttct agtttggcca agtgggggct
actctctagt tgtgatactt ggcctctca ttacggtgnc ttctttttgt tgtgggagcat ggnctctaag
gctcttgggc ttcagtagtt gcacctccca gcctgtagag cacaggcttg agagcgtggt gcagggctta
gttgctctga ggcatgtggg atcttcccag atcagggatc gaaccatgt ctcctgcatt ggcagacaga
gtctttacca ctgagccacc agggaagccc tgtgcactca cattcttgac cacatatata ccaagacaca
```

FIG. 2 CONT'D

```
gctgtccaca ggggtggcgc aggacaccct agccttagga taccccatc ttgcctgcag
GGTAAGCTCTACCGCACCAACAACACTGTGATGACCATGGCTCAGACTTCCAGTACGAGAATGCCAACACGTGGTTCA
AAAA TCTTGACAAGCTCATCCAGTTGGTCAATGCCCAG gt gagtgtgcctg/cccgtggga/c
actg/tgtt/attg/t gtt/atcccagg gt/cttg/tgggtc acatacatta tctataggtg cta/gccttagt
tttctatact taataagcta ccacaaactt agtggcttaa aacaatagcaaggatata ccttacagtt
ctgtaggtca caagtctgac atgggtctca ctgggctaaa atcaagatgt tagcagggct gtgttctnct
ggaagctcta ggggaaagtc tccttggctc atccagcttc *   attantantc cctncccnag
aatgtcatat ttcaattctc catncaagtt ttaagtaata aaattggaat attgaaagtt tagtaaaatc
tcaggtttat tcttgcatcc ctcaatttct ctccaggcca ggctggtaat tagcttggnc caatgttcat
tttcacactt agccgttggt ttgtacttaa actgtgtatt taaaaaaaga gagaaactt gnaccaaccg
ggtgcatgaa tgtgtgtgcc tgtgttttgtg tgcatgtgca cacctgtggg ccgcccggg aagggctccc
gagggctcac ataggcacac ctccccctcag CAACGGGCCAACGGGATCCGCGT CAATG
TTCTCTACTCTCTCGGCCTGTTACCTCTGGGAGC TGAACAAGGCCAACCTCAGCTG gtatttggg
ggactgggga gcctcggggg gttggcatgc cctgtgggtc ctgccctgc gtgccctgc cccaatgtc tctgctgctg
cagGTCAGTGAAAAAGGATGACTTCTTCCCCTATGCTGATGGCCCCTACATGTTCTGGACCGGTTACTTTTCA
GCCGGCCTGCCCTGCCCTCAAACGCTACGAGCGTCTCAGCTACAATTTCCTGCAG gtaggtggac gccaggctcc
aggggctggc ccaggggtcc tgacaggact ggtgcccccaa cataccacct gctccacag
GTGTGCAACCAGCTGGAGGCGCTGGCGGGTCCGGGGTCCGGCCAACGTGGACCCTATGCTCCGGGACAGTGCACCCCTCA
gtaggtgtcg gcgggcgagg ggacagcggg gtgggactga agctggactc cagacttcta ctgtccctt
cttaaagcct ttaagaaccc agcctgccag actttcgca tgtcccttggg gtctgggccg agagtcctgc
ggagacctca cttaggctac accgtctggc tacagATGAGGCGATGCCGTGCTCC
AGCACCATGATGCAGTCAGTGGTACCTCCCGGCAGCAGT
GGCTAACGACTATGCCCGCCAACTTTCAGAAGCTGGAGGCCTTGCCGAGtgtgaggggtggggcctggggaggcggag
acaggaaggactggacctggacacggggcggaaggtggtggggcggaaggtggtgggggcggggggggtcgg
acttaggaaggggcgtggtcgaaaaacagccgccagaagggctcgtggggcggggcttgtgaaaggaggacggagag
aggcagggcgggctgagagcgggatcgcgaggagacggagggcgtccagagtggaactttgttacacgcct
ccccag GTTCTCATGAGCAATGCGCT GGCGCATCTCAGCGGCTTAAAGGAGGACTTCGCCT
TTGTCGCAAGCTCAACATCAGCATTTGTCCACTCACGCAGACAGCAGAGA gtgagccggc ctggagcggg
agaggcggg ctgggggcag gtccgtggg tggtgggtgg aacgagaacc agagaaacct ctgggcccag
tgaaaaggag gagggggctga tgggggctcagc tggggctcagc tggttactga gcactctggg gcaagatatt tgagggctca
```

FIG. 2 CONT'D

```
gtgaagctgg ggcaggacgg ggaccaatgc accacttgga ggcttgactc accagggac gttgctgcat
acgtgggtgg gtttgcagaa ggcctgttgt gaccgtgtc ggctctgtcc atcccaccc ag TTCCAGG
TGATCGTTTATAACCCCTGGGGCGAAAGTGGACTGGAGGTGCGGCTGCCTGTCAGCAAACACGTTTACCTCG
TGAAGGACCCCGGTGGCAAAATTGTGCCCAGCGAT gttaaccat tctccttacc catganattc * taaataatt
cttaataataccaccccct tgaaaccccc ctcatggcat tctccttacc catganattc * taaataatt
tcccttctgc tcctttaaat cataaccccc ttgggaacat tcctgcccct cgcctatgag tatctcccc
ttgttaatat ctccctgtga aaaaatttcc tgtttatgaa tattctcctc atcctgagga cctctccctc
ctaaccactt cctccccca gaatctgttt ttccctcctt ccctgtctc aagagtctct tcccacgctt
aactcctca cttctcccac ttcctacggt agtccacc tctggtaga ttccacct tctgaatctt
ggaatctgtt tctcttttt tggccatgca gctggcaaga tcttagttcc ccaccaggg gtcaaactng
tgtccctgc agtggatgtg gagtctaacc actggactgc cagggaattc cctctttgcc atctttaact
cagcattct gacactccca ccctctctgc ccaacaccta aattctttt cccatctgg caggtgtgac
tccttgccct cctcaagttt gaccccttcc tgttttgtg gtgtggcttc atgcatgtcc tcccagcttc
ttgacttggt ttcttcctcc cttacctgag GTGGTGACCATTCCCAGTT
CAGACAGTCAGAGAGCTGCTTTTCTCAGCCTTAGTGCCTGCCGTGGGCTTCAGCATCTACTCAGTCTCCCAGATGC
CTAACCAAAGACCCCAGAAGTCCTGGTCCCGTG ACTTGGTCATCCAGAATGAG gtgagaccct actcagaccc
ccttccattt ctgggtgata gttttgagat gtggcagtaa gccacatga ctgtgggtga gtgggcgtga
agtttatggt cttgtgtcat cagtcctcca ctgtatgttc tcagtgtcct ctcttggggc tcttatgtca
ccctgggtg acacttgata gaaatgtcag agctgatgga ggtatgggtt tgnaaattca gtgaggtgtg
tcagagacgt ggaggagta gctgtgttgg tcatttgggg gtaagagaga tccagtcagg cagggagcac
cctcaagttg gnaggtgtt gggttgttca aaagacantc aattgtgttc * tgtgggtccc tcnttcaatt
tcaccaana anccctgggtc cccaanaaga tggagaaggn aaggccatgg gaagtgggga agaagtggtc
aagattgagg attagggaag aaaatggacc tgtaagattt cctnccagtg atgcacaatg agagagagag
aggagggaag ggtgggtgga ccttattttc ccaaccaggg attgaacact ctccttctac catgcaagct
gtgagtctaa atcaccccgtc tgccaggaa ttcccactt gcagtcttta attcagcatt tcagacatgc
gatccttcct gcccaacacc agtgttttgct cctgatccct gggaagaacc attggttgaa gtgatggtca
ttaatgtctg tccaccctt tactcccag TACCTCCGGGCTAGGTTTGACCCTAACACAG
GGCTCTTGATGGAGTTGGAGAACCTGGAGCAGAATCTCTTGCTGCCTGTTGCGCCAAGCCTTCTACTG gtgagagagg
accaccaggt caggggggtgg ggtgtgtgaa cagagctgag gtccctttgtc tgactctcac ctgccctggc
cctag GTACAACGCCAGTACAGGTAACAACCTAAGCTCCCAGGCCTCCGGTGCCTACATCTTC
AGACCCAACCAGAACAAACCACTGTTCGTGAGCCACTGGGCTCAGACCTCCACCTTGTG AAG gtcagggggc
```

FIG. 2 CONT'D

```
tgagagtggn nacttgggga angggngtnn aggntgggt gnatgtggng cgtgatgtgc cttgtgaggg
gtggtgggga gaatttacat ctccaataga taagaaggct aagaccagag gggaatactt gaggatttc
acacaggtt gataatcaca gctgttgta tgacagttac acatggaggc ccatagaaag gcatttcaca
tctgtcgtgg ggatcaggag tgtacttagc tttgaaatt ggtgggtagg cttgttccca tttgncct
gaatgcacag agtcaagtgt aacttgcctg aaaatttcaa tagggatctt cgataggaag * cccanaatt
tccaaaaacc ctggaaagga ccatggcaaa ngcannggtt naaanataaa ancncttgac cactaacaca
aatctggcac caagattnat ccacaccca aaaacttant tgccattgct tgaggaaaaa atcanttnat
gttttgttgc caagcaccna acctagcaag ataggggagg tgggctggcc cccgaaccta ttaagtgggg
ttgaccctga cgtaggcctt tgtgatcttc acanctgggg tggacatttg cagggctcac ctttgctcag
gtgcacgctt acacctgccc ccactcccgt gtgcccacag
GCGTCCTTGGTGCAGGAAGTACACCAGAACTTCTCAGCCTGGTGTTCCCAGTGGTTCGCCTGTATCCCAGAC
AACGGCACCTGGAGCTAGAGTGGACAGTGGGGCCCAATACCCTGTGGG gtgagcgggg ctggggctg ggggaaggnc
aaagtgaggt taaagtgaag ctcaccacct tgggtatag AGACGGCTGG
GGGAAGGAGGTCATCAGTGCCTTTGACACTGGCATTGGCGACACGCGGACTCTTCTACACTGACAGCAATGCC
GGGAGATCCTGGAGAGGAG gtggagagac tggggcacc gagggtggt ctgtggtgtg ctgggccca
gggcagtgag gggcatctg ctgatcctaa tgactgtggg aggagagga tgaaggagga gtgggtgagt
gggggaagg gaaccagact ccaagcctga tcnaatccta acccacccc agGCGGAATTATAGACCTAC
CTGGAAGCTGAACCAGACTGAACCCGTGGCTGGAAATTACTATCCAGTCAACAGCCGCATTTACACTACG
gtaccatcc cccaccctgc tccccacctt ttcctgacac ccctttacag agtggactc acctgttctt
gacatctccc aactgtcctc agcagtctcc accatccctg tgggcctgc ctgggagccg ggctggcca
gcagtgcagc ccctcactca cccttaccc ctcag GATGGGAACATGCAGCTGACTGTGCTCACTGACCG
GTCCCAGGGGGCAGTAGCCTGAGAGATGGCTCC TTGGAACTCATG gttagtggtc tgagcccca
tctaagtcag ggtccttcca ccagttccct tcctggcctc tacaggactt gaggcagttt cttttggtag
gtgcaccctt ggttgnggtc cgctaagct gaacctccat cctcttgtga gaaatcantc cgggtttt
caatcctac caaattccgt tcaggcctga ttacctatga * cctacccaa acttccgctc caggccctga
```

```
attaccctat gcacgcccgc aatagaacct taccgccgtc ttccctaanc cgtnttagg ncggaacccc
acatttactg gggaacccct acgttccctt cgtcgtcaac cgtttcccccc aanaatttt tttccctg
aaatcccac gtactttcac ccagtttccg gcccagaaat tggctacagg aaccctcact cttggccact
ctcccgcagGTCCACCGAAGGCTGCTGAAGGACGATGCACGCGAGTTGGGGAGCCGCTGAAC
AAGGAGGGGTCGGGGCTTTGGGTGCGAGGACGTCACCTCGTCGTGTTGGATAAGAAGGAGACTGCGGCCGCCAGGCACC
GGTTACAGGCGGAGATGGAGGTCCTGGCCCCGCAGGTGGTGCTGGCTCAAGGTGGCGCGCGCGGTATCGC
CTCGAGAAAGCCCACGCACGCAG gtgangaggc ncggcagaaa gaggacccaa ngaacgcctg cngagngagg
ggcggagttg agggcnggtt ntcctaggta naactgagng ccaactcggc *  ttgnggttga ccaggcctcc
tgatcngggt tgagcncncc cttctgaatt gtatcaccce ctcctgtanc gtctcanccc cgccctccc
ggctcagcce cgcccccgtc tttccctcag TTCTCTGGGCTCCGCCG CGAGCTGC
CACCCTCGGTACGTCTGCTCACATTGGCCCTGGGCCCGGAGACACTGTCTGCTGCGCTTAGA
GCACCAGTTCGCGCCGTAGGGGAGGACTCGGGCGCCCGGAACTTGAGCTCCCCGTGACCCTGGACTTGACG gtgaggatag
agatggaaag gagactgggg agaggaggga agaggaggga ggggaaaccc cgcttngtnc caacgcatcc gggcccccttc
actgcccgcag AACTTGTTTTCCGCCTTCACCATCACCAACCTGCGGGAGACCACGCTGGC
GGCCAACCAGCTCCTGGCCTTACGCGCTCCAGGCTCCAGTGGACGACGGACACGG gtaggagcct gcccggagcg
gggtggcggc cgggggtccg gngagggggg cggcggntca gtgtggagg tgcgggaatg ttgacccggt
ccaggtatag agcttggagg gtcggagtaa gtcggtgttc agattggt tagggtta agggagtgat
gtggcttgac agtccttgag gggtggact gtgggtgtga ggacagtgcc cagacactgg ggagagatt
gagcatctgg ggggtgtatc taggctctgg caaacagttg aaggggtctgg gagtgaggnc ctggggga
aag atttaaancg gtatgtctgt gttcagggga ggncgcacag aggatgttaa gncggaggaa
gtctgcatcc ntcacttctc ccctccacct cnccag GCCCCACACCCCATCCTTCCTTCCCGTCCGT
GTCCGCCACCATCACGCTGCAGCCCATGGAAATCCGTACCTTCTTGGCTTCGGTCCAATGGGAAGAGGACGG
CTAGACCCACTGGATACAAGACTACCGGCTTCTCCGAGCCCTGAGTTCTCTCTCCGGGGCGGAGC
CAACTCTCCCCCTTGTTGCTCTTACTACCACCAATGAAAGCC ATTAAAATGTCACTACCG
```

FIG. 2 CONT'D

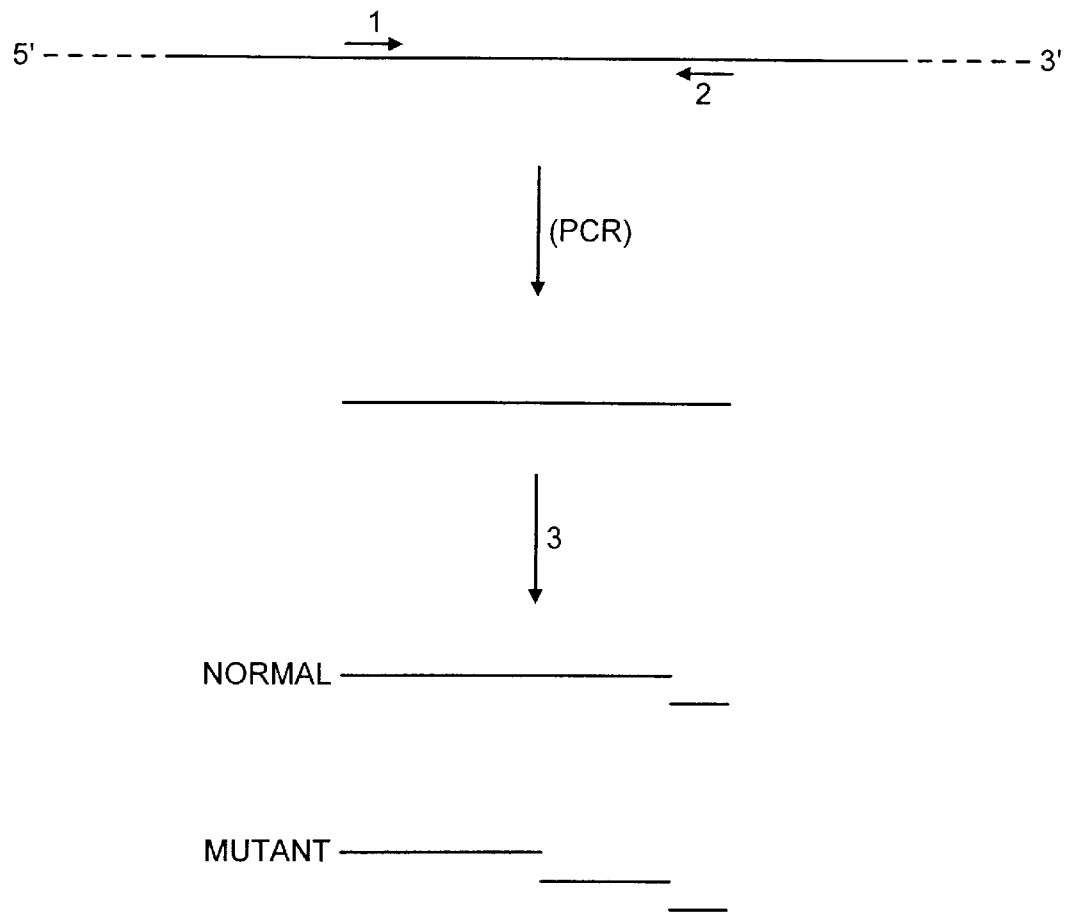

FIG. 3

```
Primer 1
5'cgctggacac    cctagcctta    ggaTACCCCC    GTCTTGCCTG    CAGGGTAAGC
   TCTACCGCAC    CAAACACACT    GTGATGACCA    TGGGCTCAGA    CTTCCAGTAC
   GAGAATGCCA    ACACGTGGTT    CAAAAATCTT    GACAAGCTCA    TCCAGTTGGT
   CAATGCCCAG    GTGAGTGTGC    CTCCCCGTGG    GCACTTGTAT    TTGTATCCCA
   GGGCTTTGGG    TCACATACAT    TATCTATAGG    TGCTGCCTTA    GTTTTCTATA
   CCTTAATAAG    CTACCACAAA    CTTAGTGGCT    TAAAACAATA    GCAAGG3'
                 tggtgttt     gaatctccga    attttgttat    cgttcc
                                             Primer 2
```

FIG. 4

| Exon # | Exon size (bp) | Sequence of intron-exon junction 5'border | 3'border | Intron size (bp) | Position of intron |
|---|---|---|---|---|---|
| 1 | >162 | GGGATACAAGgtgagcgcgg... | ...ccctgtgcagACATGCCCGA | 673 | 162 |
| 2 | 103 | TTCTATGGCAgtgagtagag... | ...gtgcccacagTCTACAATAA | 177 | 265 |
| 3 | 174 | GTGCGCCAGGgtgagcctcc... | ...cccgcacagGACGCCTAGA | 384 | 439 |
| 4 | 194 | GTTCGCGCAGgtttcagat... | ...ccanctccagATGGGTTTTG | 650* | 633 |
| 5 | 133 | CTCTTCACCAgtaaggtgt... | ...tggtccgcagGTGTGCTCCC | 220 | 766 |
| 6 | 146 | CACTGACCAGgtaaccgggt... | ...ttgcctgcagGGTAAGCTCT | 800* | 912 |
| 7 | 117 | CAATGCCCAGgtgagtgtgc... | ...ctccccctcagCAACGGGCCA | 3800* | 1029 |
| 8 | 86 | ACCTCAGCTGgtatttgggg... | ...gctgctgcagGTCAGTGAAA | 83 | 1115 |
| 9 | 121 | TTTCCTGCAGgtaggtggac... | ...tgctccacagGTGTGCAACC | 79 | 1236 |
| 10 | 79 | GCACCCCTCAgtaggtgtcg... | ...ctggctacagATGAGGCGAT | 175 | 1315 |
| 11 | 110 | GCCTTGCGAGgtgtgagggt... | ...gcctcccccagGTTCTCATGA | 250* | 1425 |
| 12 | 108 | AGCAGAGAGAgtgagccggc... | ...cccaccccagTTCCAGGTGA | 292 | 1533 |
| 13 | 117 | GCCCAGCGATgttaacccat... | ...cttacctgagGTGGTGACCA | 850* | 1650 |
| 14 | 147 | CCAGAATGAGgtgagaccct... | ...tactcccagTACCTCCGGG | 1000* | 1797 |
| 15 | 98 | CCTTCTACTGgtgagagagg... | ...ctggcctagGTACAACGCC | 85 | 1895 |
| 16 | 118 | CCTTGTGAAGgtcagggggc... | ...gtgcccacagGCGTCCTTGG | 1750* | 2013 |
| 17 | 119 | TACCTGTGGGgtgagcgggg... | ...ttggntatagAGAGACGGCTGG | 80 | 2132 |
| 18 | 102 | TGGAGAGGAGgtggagagac... | ...cccaccccagGCGGAATTAT | 172 | 2234 |
| 19 | 88 | TTACATCACGgtaaccatcc... | ...tacccctcagGATGGGAACA | 175 | 2322 |
| 20 | 81 | GGAACTCATGgttagtggtc... | ...ctcccgcagGTGCACCGAA | 410* | 2403 |
| 21 | 228 | ACGCACGCAGgtgangaggc... | ...tttccctcagTTCTCTGGGC | 450* | 2631 |
| 22 | 156 | GGACTTGACGgtgaggatag... | ...ctgcccgcagAACTTGTTTT | 91 | 2787 |
| 23 | 103 | ACGGACACGGgtaggagcct... | ...acctcnccagGCCCCACACC | 396 | 2890 |
| 24 | >227 | | | | |
| Tot: | 3117 | | | 13042 | |

* approximate size

FIG. 10

SEQUENCE LISTING (1) GENERAL INFORMATION:

(iii) NUMBER OF SEQUENCES: 104

(2) INFORMATION FOR SEQ ID NO:1:

(i) SEQUENCE CHARACTERISTICS:
      (A) LENGTH: 3147 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO -continued

```
    (ix) FEATURE:
         (A) NAME/KEY: CDS
         (B) LOCATION: 15..3011

(ix) FEATURE:
         (A) NAME/KEY: polyA_signal
         (B) LOCATION: 3115..3120

(xi) SEQUENCE DESCRIPTION: SEQ ID NO:1:

GCGGCTGCAG AGCC ATG GTT GGT GAC GCG CGG CCT TCA GGG GTT CGC GCT          50
              Met Val Gly Asp Ala Arg Pro Ser Gly Val Arg Ala
                1               5                  10

GGC GGC TGC CGG GGC GCG GTA GGA TCC CGG ACG AGC TCC CGC GCG CTG          98
Gly Gly Cys Arg Gly Ala Val Gly Ser Arg Thr Ser Ser Arg Ala Leu
            15                  20                  25

CGG CCA CCG CTC CCG CCT CTC TCC TCC CTC TTC GTG TTG TTC CTA GCG         146
Arg Pro Pro Leu Pro Pro Leu Ser Ser Leu Phe Val Leu Phe Leu Ala
        30                  35                  40

GCG CCC TGC GCT TGG GCG GCG GGA TAC AAG ACA TGC CCG AAG GTG AAG         194
Ala Pro Cys Ala Trp Ala Ala Gly Tyr Lys Thr Cys Pro Lys Val Lys
    45                  50                  55                  60

CCG GAC ATG CTG AAT GTA CAC CTG GTG CCT CAC ACA CAT GAT GAT GTA         242
Pro Asp Met Leu Asn Val His Leu Val Pro His Thr His Asp Asp Val
                65                  70                  75

GGC TGG CTC AAG ACG GTG GAC CAG TAC TTC TAT GGC ATC TAC AAT AAC         290
Gly Trp Leu Lys Thr Val Asp Gln Tyr Phe Tyr Gly Ile Tyr Asn Asn
            80                  85                  90

ATC CAG CCG GCG GGT GTA CAG TAC ATC CTA GAC TCC GTC ATC TCT TCC         338
Ile Gln Pro Ala Gly Val Gln Tyr Ile Leu Asp Ser Val Ile Ser Ser
        95                  100                 105

TTG CTG GCG AAT CCC ACC CGC CGC TTC ATC TAT GTG GAA ATC GCC TTC         386
Leu Leu Ala Asn Pro Thr Arg Arg Phe Ile Tyr Val Glu Ile Ala Phe
110                 115                 120

TTC TCG CGT TGG TGG CGC CAG CAG ACA AAT GCA ACA CAG AAA ATC GTG         434
Phe Ser Arg Trp Trp Arg Gln Gln Thr Asn Ala Thr Gln Lys Ile Val
125                 130                 135                 140

AGG GAA CTG GTG CGC CAG GGA CGC CTA GAG TTC GCC AAC GGT GGC TGG         482
Arg Glu Leu Val Arg Gln Gly Arg Leu Glu Phe Ala Asn Gly Gly Trp
                145                 150                 155

GTG ATG AAC GAT GAG GCG ACC ACC CAC TAC GGA GCC ATC ATT GAC CAG         530
Val Met Asn Asp Glu Ala Thr Thr His Tyr Gly Ala Ile Ile Asp Gln
            160                 165                 170

ATG ACA CTC AGA CTG CGC TTC CTG GAG GAG ACG TTC GGC AGC GAC GGG         578
Met Thr Leu Arg Leu Arg Phe Leu Glu Glu Thr Phe Gly Ser Asp Gly
        175                 180                 185

CGC CCC CGT GTG GCC TGG CAC ATC GAC CCA TTC GGC CAC TCT CGG GAG         626
Arg Pro Arg Val Ala Trp His Ile Asp Pro Phe Gly His Ser Arg Glu
    190                 195                 200

CAA GCT TCA CTG TTC GCG CAG ATG GGT TTT GAC GGC TTC TTC TTT GGA         674
Gln Ala Ser Leu Phe Ala Gln Met Gly Phe Asp Gly Phe Phe Phe Gly
205                 210                 215                 220

CGC CTG GAT TAT CAA GAC AAG AAG GTG CGG AAA AAG ACG CTG CAG ATG         722
Arg Leu Asp Tyr Gln Asp Lys Lys Val Arg Lys Lys Thr Leu Gln Met
                225                 230                 235

GAG CAG GTG TGG CGG GCC AGC ACC AGC CTG AAA CCT CCC ACT GCC GAC         770
Glu Gln Val Trp Arg Ala Ser Thr Ser Leu Lys Pro Pro Thr Ala Asp
            240                 245                 250

CTC TTC ACC AGT GTG CTC CCC AAC ATG TAC AAC CCG CCG GAA GGT CTG         818
Leu Phe Thr Ser Val Leu Pro Asn Met Tyr Asn Pro Pro Glu Gly Leu
        255                 260                 265
```

```
                                                          -continued

TGC TGG GAC ATG CTG TGT GCC GAC AAG CCG GTT GTG GAG GAC ACG CGT      866
Cys Trp Asp Met Leu Cys Ala Asp Lys Pro Val Val Glu Asp Thr Arg
    270                 275                 280

AGC CCA GAG TAC AAC GCA AAA GAG CTG GTC CGT TAC TTC CTG AAG TTG      914
Ser Pro Glu Tyr Asn Ala Lys Glu Leu Val Arg Tyr Phe Leu Lys Leu
285                 290                 295                 300

GCC ACT GAC CAG GGT AAG CTC TAC CGC ACC AAA CAC ACT GTG ATG ACC      962
Ala Thr Asp Gln Gly Lys Leu Tyr Arg Thr Lys His Thr Val Met Thr
                    305                 310                 315

ATG GGC TCA GAC TTC CAG TAC GAG AAT GCC AAC ACG TGG TTC AAA AAT     1010
Met Gly Ser Asp Phe Gln Tyr Glu Asn Ala Asn Thr Trp Phe Lys Asn
                320                 325                 330

CTT GAC AAG CTC ATC CAG TTG GTC AAT GCC CAG CAA CGG GCC AAC GGG     1058
Leu Asp Lys Leu Ile Gln Leu Val Asn Ala Gln Gln Arg Ala Asn Gly
            335                 340                 345

ATC CGC GTC AAT GTT CTC TAC TCT ACC TCG GCC TGT TAC CTC TGG GAG     1106
Ile Arg Val Asn Val Leu Tyr Ser Thr Ser Ala Cys Tyr Leu Trp Glu
        350                 355                 360

CTG AAC AAG GCC AAC CTC AGC TGG TCA GTG AAA AAG GAT GAC TTC TTC     1154
Leu Asn Lys Ala Asn Leu Ser Trp Ser Val Lys Lys Asp Asp Phe Phe
365                 370                 375                 380

CCC TAT GCT GAT GGC CCC TAC ATG TTC TGG ACC GGT TAC TTT TCC AGC     1202
Pro Tyr Ala Asp Gly Pro Tyr Met Phe Trp Thr Gly Tyr Phe Ser Ser
                    385                 390                 395

CGG CCT GCC CTC AAA CGC TAC GAG CGT CTC AGC TAC AAT TTC CTG CAG     1250
Arg Pro Ala Leu Lys Arg Tyr Glu Arg Leu Ser Tyr Asn Phe Leu Gln
                400                 405                 410

GTG TGC AAC CAG CTG GAG GCG CTG GCG GGT CCG GCA GCC AAC GTG GGA     1298
Val Cys Asn Gln Leu Glu Ala Leu Ala Gly Pro Ala Ala Asn Val Gly
            415                 420                 425

CCC TAT GGC TCC GGG GAC AGT GCA CCC CTC AAT GAG GCG ATG GCC GTG     1346
Pro Tyr Gly Ser Gly Asp Ser Ala Pro Leu Asn Glu Ala Met Ala Val
        430                 435                 440

CTC CAG CAC CAT GAT GCA GTC AGT GGT ACC TCC CGG CAG CAC GTG GCT     1394
Leu Gln His His Asp Ala Val Ser Gly Thr Ser Arg Gln His Val Ala
445                 450                 455                 460

AAC GAC TAT GCC CGC CAA CTT TCA GAA GGC TGG AGG CCT TGC GAG GTT     1442
Asn Asp Tyr Ala Arg Gln Leu Ser Glu Gly Trp Arg Pro Cys Glu Val
                    465                 470                 475

CTC ATG AGC AAT GCG CTG GCG CAT CTC AGC GGC TTA AAG GAG GAC TTC     1490
Leu Met Ser Asn Ala Leu Ala His Leu Ser Gly Leu Lys Glu Asp Phe
                480                 485                 490

GCC TTT TGT CGC AAG CTC AAC ATC AGC ATT TGT CCA CTC ACG CAG ACA     1538
Ala Phe Cys Arg Lys Leu Asn Ile Ser Ile Cys Pro Leu Thr Gln Thr
            495                 500                 505

GCA GAG AGA TTC CAG GTG ATC GTT TAT AAC CCC CTG GGG CGG AAA GTG     1586
Ala Glu Arg Phe Gln Val Ile Val Tyr Asn Pro Leu Gly Arg Lys Val
        510                 515                 520

GAC TGG ATG GTG CGG CTG CCT GTC AGC AAA CAC GTT TAC CTC GTG AAG     1634
Asp Trp Met Val Arg Leu Pro Val Ser Lys His Val Tyr Leu Val Lys
525                 530                 535                 540

GAC CCC GGT GGC AAA ATT GTG CCC AGC GAT GTG GTG ACC ATT CCC AGT     1682
Asp Pro Gly Gly Lys Ile Val Pro Ser Asp Val Val Thr Ile Pro Ser
                    545                 550                 555

TCA GAC AGT CAG GAG CTG CTT TTC TCA GCC TTA GTG CCT GCC GTG GGC     1730
Ser Asp Ser Gln Glu Leu Leu Phe Ser Ala Leu Val Pro Ala Val Gly
                560                 565                 570

TTC AGC ATC TAC TCA GTC TCC CAG ATG CCT AAC CAA AGA CCC CAG AAG     1778
Phe Ser Ile Tyr Ser Val Ser Gln Met Pro Asn Gln Arg Pro Gln Lys
            575                 580                 585
```

```
TCC TGG TCC CGT GAC TTG GTC ATC CAG AAT GAG TAC CTC CGG GCT AGG    1826
Ser Trp Ser Arg Asp Leu Val Ile Gln Asn Glu Tyr Leu Arg Ala Arg
    590                 595                 600

TTT GAC CCT AAC ACA GGG CTC TTG ATG GAG TTG GAG AAC CTG GAG CAG    1874
Phe Asp Pro Asn Thr Gly Leu Leu Met Glu Leu Glu Asn Leu Glu Gln
605                 610                 615                 620

AAT CTC TTG CTG CCT GTT CGC CAA GCC TTC TAC TGG TAC AAC GCC AGT    1922
Asn Leu Leu Leu Pro Val Arg Gln Ala Phe Tyr Trp Tyr Asn Ala Ser
                625                 630                 635

ACA GGT AAC AAC CTA AGC TCC CAG GCC TCC GGT GCC TAC ATC TTC AGA    1970
Thr Gly Asn Asn Leu Ser Ser Gln Ala Ser Gly Ala Tyr Ile Phe Arg
        640                 645                 650

CCC AAC CAG AAC AAA CCA CTG TTC GTG AGC CAC TGG GCT CAG ACC CAC    2018
Pro Asn Gln Asn Lys Pro Leu Phe Val Ser His Trp Ala Gln Thr His
    655                 660                 665

CTT GTG AAG GCG TCC TTG GTG CAG GAA GTA CAC CAG AAC TTC TCA GCC    2066
Leu Val Lys Ala Ser Leu Val Gln Glu Val His Gln Asn Phe Ser Ala
    670                 675                 680

TGG TGT TCC CAG GTG GTT CGC CTG TAT CCC AGA CAA CGG CAC CTG GAG    2114
Trp Cys Ser Gln Val Val Arg Leu Tyr Pro Arg Gln Arg His Leu Glu
685                 690                 695                 700

CTA GAG TGG ACA GTG GGG CCA ATA CCT GTG GGA GAC GGC TGG GGG AAG    2162
Leu Glu Trp Thr Val Gly Pro Ile Pro Val Gly Asp Gly Trp Gly Lys
                705                 710                 715

GAG GTC ATC AGT CGC TTT GAC ACT GCA TTG GCG ACA CGC GGA CTC TTC    2210
Glu Val Ile Ser Arg Phe Asp Thr Ala Leu Ala Thr Arg Gly Leu Phe
            720                 725                 730

TAC ACT GAC AGC AAT GGC CGG GAG ATC CTG GAG AGG AGG CGG AAT TAT    2258
Tyr Thr Asp Ser Asn Gly Arg Glu Ile Leu Glu Arg Arg Arg Asn Tyr
        735                 740                 745

AGA CCT ACC TGG AAG CTG AAC CAG ACT GAA CCC GTG GCT GGA AAT TAC    2306
Arg Pro Thr Trp Lys Leu Asn Gln Thr Glu Pro Val Ala Gly Asn Tyr
    750                 755                 760

TAT CCA GTC AAC AGC CGC ATT TAC ATC ACG GAT GGG AAC ATG CAG CTG    2354
Tyr Pro Val Asn Ser Arg Ile Tyr Ile Thr Asp Gly Asn Met Gln Leu
765                 770                 775                 780

ACT GTG CTC ACT GAC CGG TCC CAG GGG GGC AGT AGC CTG AGA GAT GGC    2402
Thr Val Leu Thr Asp Arg Ser Gln Gly Gly Ser Ser Leu Arg Asp Gly
                785                 790                 795

TCC TTG GAA CTC ATG GTG CAC CGA AGG CTG CTG AAG GAC GAT GCA CGC    2450
Ser Leu Glu Leu Met Val His Arg Arg Leu Leu Lys Asp Asp Ala Arg
            800                 805                 810

GGA GTT GGG GAG CCG CTG AAC AAG GAG GGG TCG GGG CTT TGG GTG CGA    2498
Gly Val Gly Glu Pro Leu Asn Lys Glu Gly Ser Gly Leu Trp Val Arg
        815                 820                 825

GGA CGT CAC CTC GTG CTG TTG GAT AAG AAG GAG ACT GCG GCC GCC AGG    2546
Gly Arg His Leu Val Leu Leu Asp Lys Lys Glu Thr Ala Ala Ala Arg
    830                 835                 840

CAC CGG TTA CAG GCG GAG ATG GAG GTC CTG GCC CCG CAG GTG GTG CTG    2594
His Arg Leu Gln Ala Glu Met Glu Val Leu Ala Pro Gln Val Val Leu
845                 850                 855                 860

GCT CAA GGT GGC GGC GCG CGG TAT CGC CTC GAG AAA GCC CCA CGC ACG    2642
Ala Gln Gly Gly Gly Ala Arg Tyr Arg Leu Glu Lys Ala Pro Arg Thr
                865                 870                 875

CAG TTC TCT GGG CTC CGC CGC GAG CTG CCA CCC TCG GTA CGT CTG CTC    2690
Gln Phe Ser Gly Leu Arg Arg Glu Leu Pro Pro Ser Val Arg Leu Leu
            880                 885                 890

ACA TTG GCC CGC TGG GGC CCG GAG ACA CTG CTG CTG CGC TTA GAG CAC    2738
Thr Leu Ala Arg Trp Gly Pro Glu Thr Leu Leu Leu Arg Leu Glu His
        895                 900                 905
```

-continued

```
CAG TTC GCC GTA GGG GAG GAC TCG GGC CGG AAC TTG AGC TCC CCG GTG        2786
Gln Phe Ala Val Gly Glu Asp Ser Gly Arg Asn Leu Ser Ser Pro Val
        910                 915                 920

ACC CTG GAC TTG ACG AAC TTG TTT TCC GCC TTC ACC ATC ACC AAC CTG        2834
Thr Leu Asp Leu Thr Asn Leu Phe Ser Ala Phe Thr Ile Thr Asn Leu
925                 930                 935                 940

CGG GAG ACC ACG CTG GCG GCC AAC CAG CTC CTG GCC TAC GCC TCC AGG        2882
Arg Glu Thr Thr Leu Ala Ala Asn Gln Leu Leu Ala Tyr Ala Ser Arg
                945                 950                 955

CTC CAG TGG ACG ACG GAC ACG GGC CCC ACA CCC CAT CCT TCT CCT TCC        2930
Leu Gln Trp Thr Thr Asp Thr Gly Pro Thr Pro His Pro Ser Pro Ser
            960                 965                 970

CGT CCG GTG TCC GCC ACC ATC ACG CTG CAG CCC ATG GAA ATC CGT ACC        2978
Arg Pro Val Ser Ala Thr Ile Thr Leu Gln Pro Met Glu Ile Arg Thr
        975                 980                 985

TTC TTG GCT TCG GTC CAA TGG GAA GAG GAC GGC TAGACCCACT GGATACAAGA     3031
Phe Leu Ala Ser Val Gln Trp Glu Glu Asp Gly
        990                 995

CTACCGGCTC CGAGCCTGAG TTCTCTCTCC GGGGGCGGAG CCAACTCTCC CCCTTGTTGC      3091

TCTTACTACC ACCAATGAAA GCCATTAAAA TGTCACTACC GAAAAAAAAA AAAAAA         3147

(2) INFORMATION FOR SEQ ID NO:2:

(i) SEQUENCE CHARACTERISTICS:
        (A) LENGTH: 999 amino acids
        (B) TYPE: amino acid
        (C) STRANDEDNESS: Not Relevant
        (D) TOPOLOGY: Not Relevant (ii) MOLECULE TYPE: protein (iii) HYPOTHETICAL: not relevant (iv) ANTI-SENSE: not relevant (xi) SEQUENCE DESCRIPTION: SEQ ID NO:2:

Met Val Gly Asp Ala Arg Pro Ser Gly Val Arg Ala Gly Gly Cys Arg
1               5                   10                  15

Gly Ala Val Gly Ser Arg Thr Ser Ser Arg Ala Leu Arg Pro Pro Leu
            20                  25                  30

Pro Pro Leu Ser Ser Leu Phe Val Leu Phe Leu Ala Ala Pro Cys Ala
        35                  40                  45

Trp Ala Ala Gly Tyr Lys Thr Cys Pro Lys Val Lys Pro Asp Met Leu
    50                  55                  60

Asn Val His Leu Val Pro His Thr His Asp Asp Val Gly Trp Leu Lys
65                  70                  75                  80

Thr Val Asp Gln Tyr Phe Tyr Gly Ile Tyr Asn Asn Ile Gln Pro Ala
                85                  90                  95

Gly Val Gln Tyr Ile Leu Asp Ser Val Ile Ser Ser Leu Leu Ala Asn
            100                 105                 110

Pro Thr Arg Arg Phe Ile Tyr Val Glu Ile Ala Phe Phe Ser Arg Trp
        115                 120                 125

Trp Arg Gln Gln Thr Asn Ala Thr Gln Lys Ile Val Arg Glu Leu Val
    130                 135                 140

Arg Gln Gly Arg Leu Glu Phe Ala Asn Gly Gly Trp Val Met Asn Asp
145                 150                 155                 160

Glu Ala Thr Thr His Tyr Gly Ala Ile Ile Asp Gln Met Leu Arg Leu
                165                 170                 175
```

-continued

```
Thr Arg Phe Leu Glu Glu Thr Phe Gly Ser Asp Gly Arg Pro Arg Val
            180                 185                 190

Ala Trp His Ile Asp Pro Phe Gly His Ser Arg Glu Gln Ala Ser Leu
            195                 200                 205

Phe Ala Gln Met Gly Phe Asp Gly Phe Phe Gly Arg Leu Asp Tyr
            210                 215                 220

Gln Asp Lys Lys Val Arg Lys Lys Thr Leu Gln Met Glu Gln Val Trp
225                 230                 235                 240

Arg Ala Ser Thr Ser Leu Lys Pro Pro Thr Ala Asp Leu Phe Thr Ser
                245                 250                 255

Val Leu Pro Asn Met Tyr Asn Pro Pro Glu Gly Leu Cys Trp Asp Met
            260                 265                 270

Leu Cys Ala Asp Lys Pro Val Val Glu Asp Thr Arg Ser Pro Glu Tyr
            275                 280                 285

Asn Ala Lys Glu Leu Val Arg Tyr Phe Leu Lys Leu Ala Thr Asp Gln
            290                 295                 300

Gly Lys Leu Tyr Arg Thr Lys His Thr Val Met Thr Met Gly Ser Asp
305                 310                 315                 320

Phe Gln Tyr Glu Asn Ala Asn Thr Trp Phe Lys Asn Leu Asp Lys Leu
                325                 330                 335

Ile Gln Leu Val Asn Ala Gln Gln Arg Ala Asn Gly Ile Arg Val Asn
            340                 345                 350

Val Leu Tyr Ser Thr Ser Ala Cys Tyr Leu Trp Glu Leu Asn Lys Ala
            355                 360                 365

Asn Leu Ser Trp Ser Val Lys Lys Asp Asp Phe Phe Pro Tyr Ala Asp
            370                 375                 380

Gly Pro Tyr Met Phe Trp Thr Gly Tyr Phe Ser Ser Arg Pro Ala Leu
385                 390                 395                 400

Lys Arg Tyr Glu Arg Leu Ser Tyr Asn Phe Leu Gln Val Cys Asn Gln
                405                 410                 415

Leu Glu Ala Leu Ala Gly Pro Ala Ala Asn Val Gly Pro Tyr Gly Ser
            420                 425                 430

Gly Asp Ser Ala Pro Leu Asn Glu Ala Met Ala Val Leu Gln His His
            435                 440                 445

Asp Ala Val Ser Gly Thr Ser Arg Gln His Val Ala Asn Asp Tyr Ala
            450                 455                 460

Arg Gln Leu Ser Glu Gly Trp Arg Pro Cys Glu Val Leu Met Ser Asn
465                 470                 475                 480

Ala Leu Ala His Leu Ser Gly Leu Lys Glu Asp Phe Ala Phe Cys Arg
                485                 490                 495

Lys Leu Asn Ile Ser Ile Cys Pro Leu Thr Gln Thr Ala Glu Arg Phe
            500                 505                 510

Gln Val Ile Val Tyr Asn Pro Leu Gly Arg Lys Val Asp Trp Met Val
            515                 520                 525

Arg Leu Pro Val Ser Lys His Val Tyr Leu Val Lys Asp Pro Gly Gly
            530                 535                 540

Lys Ile Val Pro Ser Asp Val Val Thr Ile Pro Ser Ser Asp Ser Gln
545                 550                 555                 560

Glu Leu Leu Phe Ser Ala Leu Val Pro Ala Val Gly Phe Ser Ile Tyr
                565                 570                 575

Ser Val Ser Gln Met Pro Asn Gln Arg Pro Gln Lys Ser Trp Ser Arg
            580                 585                 590
```

-continued

Asp Leu Val Ile Gln Asn Glu Tyr Leu Arg Ala Arg Phe Asp Pro Asn
            595                 600                 605

Thr Gly Leu Leu Met Glu Leu Glu Asn Leu Glu Gln Asn Leu Leu Leu
610                 615                 620

Pro Val Arg Gln Ala Phe Tyr Trp Tyr Asn Ala Ser Thr Gly Asn Asn
625                 630                 635                 640

Leu Ser Ser Gln Ala Ser Gly Ala Tyr Ile Phe Arg Pro Asn Gln Asn
            645                 650                 655

Lys Pro Leu Phe Val Ser His Trp Ala Gln Thr His Leu Val Lys Ala
            660                 665                 670

Ser Leu Val Gln Glu Val His Gln Asn Phe Ser Ala Trp Cys Ser Gln
            675                 680                 685

Val Val Arg Leu Tyr Pro Arg Gln Arg His Leu Glu Leu Glu Trp Thr
            690                 695                 700

Val Gly Pro Ile Pro Val Gly Asp Gly Trp Gly Lys Glu Val Ile Ser
705                 710                 715                 720

Arg Phe Asp Thr Ala Leu Ala Thr Arg Gly Leu Phe Tyr Thr Asp Ser
            725                 730                 735

Asn Gly Arg Glu Ile Leu Glu Arg Arg Asn Tyr Arg Pro Thr Trp
            740                 745                 750

Lys Leu Asn Gln Thr Glu Pro Val Ala Gly Asn Tyr Tyr Pro Val Asn
            755                 760                 765

Ser Arg Ile Tyr Ile Thr Asp Gly Asn Met Gln Leu Thr Val Leu Thr
            770                 775                 780

Asp Arg Ser Gln Gly Gly Ser Ser Leu Arg Asp Gly Ser Leu Glu Leu
785                 790                 795                 800

Met Val His Arg Arg Leu Leu Lys Asp Asp Ala Arg Gly Val Gly Glu
            805                 810                 815

Pro Leu Asn Lys Glu Gly Ser Gly Leu Trp Val Arg Gly Arg His Leu
            820                 825                 830

Val Leu Leu Asp Lys Lys Glu Thr Ala Ala Arg His Arg Leu Gln
            835                 840                 845

Ala Glu Met Glu Val Leu Ala Pro Gln Val Val Leu Ala Gln Gly Gly
            850                 855                 860

Gly Ala Arg Tyr Arg Leu Glu Lys Ala Pro Arg Thr Gln Phe Ser Gly
865                 870                 875                 880

Leu Arg Arg Glu Leu Pro Pro Ser Val Arg Leu Leu Thr Leu Ala Arg
            885                 890                 895

Trp Gly Pro Glu Thr Leu Leu Leu Arg Leu Glu His Gln Phe Ala Val
            900                 905                 910

Gly Glu Asp Ser Gly Arg Asn Leu Ser Ser Pro Val Thr Leu Asp Leu
            915                 920                 925

Thr Asn Leu Phe Ser Ala Phe Thr Ile Thr Asn Leu Arg Glu Thr Thr
            930                 935                 940

Leu Ala Ala Asn Gln Leu Leu Ala Tyr Ala Ser Arg Leu Gln Trp Thr
945                 950                 955                 960

Thr Asp Thr Gly Pro Thr Pro His Pro Ser Pro Ser Arg Pro Val Ser
            965                 970                 975

Ala Thr Ile Thr Leu Gln Pro Met Glu Ile Arg Thr Phe Leu Ala Ser
            980                 985                 990

Val Gln Trp Glu Glu Asp Gly
            995

(2) INFORMATION FOR SEQ ID NO:3:

(i) SEQUENCE CHARACTERISTICS:
        (A) LENGTH: 11703 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

```
GCGGCTGCAG AGCCATGGTT GGTGACGCGC GGCCTTCAGG GGTTCGCGCT GGCGGCTGCC      60
GGGGCGCGGT AGGATCCCGG ACGAGCTCCC GCGCGCTGCG GCCACCGCTC CCGCCTCTCT     120
CCTCCCTCTT CGTGTTGTTC CTAGCGGCGC CCTGCGCTTG GCGGCGGGA TACAAGGTGA     180
GCGCGGCCCG CTAGCGGAAA TGTACAAGAG CCATAGTGAA GCCTCCAGTA GAGTCGGAGG     240
TGTGTGCGTG GGTCTGTTTT GTGGGTGCCC AGTGAATGGT TGCTAATATG ACAGTGTGAT     300
CTGGTTCATG CTTTGTGTTA CTGAGAAGAC TGGCTGTGTT AGTCTGAGAA TGGGGCTGTC     360
TGTGTCTGTC TCTTGCTTCT GTGGATTGGC TTACCTGGAC TTGGCAAGCA TTTACACGAG     420
CGGGCTGTGT GGTGGGGACT GGTTGAGAGT TGGGAGTCAG CTGCCTGAAG TTTTAACCTG     480
ACTTCTCAAC TTGTGACCTT GGCCAAATCA CNTCACTTCT CTGAGCCTCT GTATTCTCAT     540
CTGAAAACTG GAGATAATGT TGCCCTCAGG TCCCAGGGTG CCTGCTTGGT ATTAACAAAT     600
GCTTAATAAA CATGAGCTAC TACTAGTGTT TTCCGAGGGC ATGAACGAGA GGTGCTCTGA     660
GAAGTTCTGT CAGTTGGGGA GTACATCTAT GACACAACTA TGTGTGTCCT TCTTAGGGGA     720
GCCGATCCCC ACCTGTCACT TGCTTCTAGA TCAAGACTTA CCTTATATCC TCCCAACCCN     780
CCACTGCAGC CTGCCTCTTA ACCTTGGAGT TACTGACAGA GTGAGTGTGT GTTTGGGGTC     840
CCTGTGCAGA CATGCCCGAA GGTGAAGCCG GACATGCTGA ATGTACACCT GGTGCCTCAC     900
ACACATGATG ATGTAGGCTG GCTCAAGACG GTGGACCAGT ACTTCTATGG CAGTGAGTAG     960
AGGAGGGTGG GGAGTGACCC CTGGGACTCC CATGGTCCTG CGGAGCCCTT AAAATTCCTT    1020
TTCAGGCCTG GACAATCAGG GTGGGGGCAA CACCCAGCTT GGGCTCCTGT GTCTAAGAAT    1080
GTTTCCCTTG GCTTGCTGAT TTCTGATTGN CTGACCCCTG TGCCCACAGT CTACAATAAC    1140
ATCCAGCCGG CGGGTGTACA GTACATCCTA GACTCCGTCA TCTCTTCCTT GCTGGCGAAT    1200
CCCACCCGCC GCTTCATCTA TGTGGAAATC GCCTTCTTCT CGCGTTGGTG GCGCCAGCAG    1260
ACAAATGCAA CACAGAAAAT CGTGAGGGAA CTGGTGCGCC AGGGTGAGCC TCCCTTCAGG    1320
AAGTGAAAAG AGGAAGCCAA GCCCAGCTTC TATCTCTAGC ACCCTGGCTT CTGAGATTTT    1380
ATCACGCCAT TTGCAGCCTC TATGTGGCTG CCGTTGCTGC TTCTGCTAAG TCGCTTCAAT    1440
CGTGTCCGAC TCTGTGTGAC CCCATAGACA GCAGCCCACG AGGCTCCCCC ATCCCTGGGA    1500
TTCTCCAGGC AAGAACACTG GAGTGGATTG TGTTCCATAG CTCTCTTACA CTGGCCTGAG    1560
AGTGACCCCT GACCCTTCTC CTCTCAGGCC TGGTCGTTTA AGCAGGTCTT CTCGTCCCTG    1620
GCATCACCAA CCCTGGCGCC ACTCCTGGCC CTGACAACTG ACTTGGACTT TGCCCCTCCC    1680
GGCACAGGAC GCCTAGAGTT CGCCAACGGT GGCTGGGTGA TGAACGATGA GGCGACCACC    1740
CACTACGGAG CCATCATTGA CCAGATGACA CTCAGACTGC GCTTCCTGGA GGAGACGTTC    1800
GGCAGCGACG GGCGCCCCCG TGTGGCCTGG CACATCGACC CATTCGGCCA CTCTCGGGAG    1860
CAAGCTTCAC TGTTCGCGCA GTGGCTGGGT GATGAACGAT GAGGCGACCA CCCACTACGG    1920
```

```
AGCCATCATC GACCAGATGA CACTCAGACT GCGCTTCCTG GAGGAGACGT TCGGCAGCGA    1980

CGGGCGCCCC CGTGTGGCCT GGCACATCGA CCCATTCGGC CACTCTCGGG AGCAAGCTTC    2040

ACTGTTCGCG CAGGTTTTCA GATCTCTTGG GCCCGCCCCT TCATTCCTTC TGACTCCTCC    2100

TCTGTCATCC AAGCCCCGCC CTTTTCTGNA AGTTCACCCG AACCCGAACC AGGCCCTACC    2160

CCTGGNCCTC TCGCCACTTA AGACCCTGCC TCTTGGGTGA CCTGTGAATC CCATTCTTTT    2220

NGGTCTGGCC TTGGTTCTGC TCTGTCCTAG NCTAGGTTGA CCTCATCAAC TATTCCCATA    2280

CAACCCGGNC TCCCTTGTCA GGTGAGTNTC CCCCTCCCTG ATCCANCCAG TTGGTCTGAT    2340

CTGGTNTTGG CAAGTGGTGG TTGTAGGGCT GGGTTTCANC AGTTCGTACT GTGCATACAC    2400

CCTCCTGTAG TNGGANGGAG CNCTGATGGA GNGGTGTGGG TGGTGTCCCG GTTCNAGGTN    2460

TACTCCAAAC ANCTTTCNTG NCTGCCTCCT TCCAACCGGG TNACCTAAAC AATCCAAAAC    2520

CCGGCNCCTT GCAATNATCT CCCCTCCCTG ATCAACAAGT TNTCTGACCT GCTCTTGCCC    2580

AACCTGGTGG CTGGTTAGGN CCTCGGTTTT TCAACCAACC TCGTTACCTG TNCCATGACC    2640

ATCCCCCTTC CCTTGCTAGG CTGCGGAAAG GGGAAGGCCT CCTAGANCTG GGGAAGGTGG    2700

AGGTGGGTTG TAGCGTTGGA CTTGCTCCCT CCCGGCGCTT CCGCAGGGCT TCTGACCTTC    2760

CTCAGCCTTT GAAATGAACT GGAGGGCCTC GCTGGTCTTT GACNTGGTTT TTCTCCCTGT    2820

GCGTGAGAGG TTGGTGGTTG GTGATGAGAG GACCGGTCCC TTATGCATCC TGCCCTCTCN    2880

TGNTCTCCCA NCCCACTCGT CATCCCTCCC CANCTCCAGA TGGGTTTTGA CGGCTTCTTC    2940

TTTGGACGCC TGGATTATCA AGACAAGAAG GTGCGGAAAA AGACGCTGCA GATGGAGCAG    3000

GTGTGGCGGG CCAGCACCAG CCTGAAACCT CCCACTGCCG ACCTCTTCAC CAGTAAGGTG    3060

GTAGAGTGGA AAGAGGSCCG CCCCCGTGCT CAGAAGGGCC CTGGGCTTGG TTTATGGTCT    3120

GCTATCATTG TCTTGAAATT CCTAGTAGTT TATGAACAGG GGCCCACCAT TTGSAGTTTG    3180

CACTGGGCCT GGCAAATTCT GAAATCCATC CCCGGTGAGG CCTGGYAGGT CTAGGGGCCA    3240

TGACCACCCC CTGAACCTAA TGTGGTCCGC AGGTGTGCTC CCCAACATGT ACAACCCGCC    3300

GGAAGGTCTG TGCTGGGACA TGCTGTGTGC CGACAAGCCG GTTGTGGAGG ACACGCGTAG    3360

CCCAGAGTAC AACGCAAAAG AGCTGGTCCG TTACTTCCTG AAGTTGGCCA CTGACCAGGT    3420

AACCGGGTGT CCAGAACCTA TGCCTCCAGT GTACACGCAC TGGGCCCTTC CATCGGCCCA    3480

GACAATCCCT AGCACTTCCT CACCTTCACT GGGGGAAGGT AAAATTCCAT TCACCATCAC    3540

CATACCCTGC TCCTGGATTT GTGTGCATTT CTGATTAGAA AGGTGGAGCC CTTCGCCAGA    3600

GCACATCCCC ACCATGTTTG NTAGACAGCA TGGNACAGGA CCTCAGTACC CATGTCTGGG    3660

TGGTAGGCCC AAGAGAATTC CTCAACCGCT TGTGGCTCTT TTTCTGTGTG TCCCTCTGCT    3720

CCCATGTGAC ACACTTCCAC CCCTACCCCC CATGGCTCTG TGCACTCACA TTCTTTTTAT    3780

TTAAAAAAAT AATTTTTGTT TTTGCCTGTA CTGGGTCCTT TGTTNCAAT CCGNACAATT     3840

TTTCTAGTTT GGCCAAGTGG GGGCTACTCT CTAGTTGTGA TACTTGGCCT TCTCATTACG    3900

GTGNCTTCTT TTTGTTGTGG AGCATGGNCT CTAAGGCTCT TGGGCTTCAG TAGTTGCACC    3960

TCCCAGCCTG TAGAGCACAG GCTTGAGAGC GTGGTGCAGG GCTTAGTTGC TCTGAGGCAT    4020

GTGGGATCTT CCCAGATCAG GGATCGAACC CATGTCTCCT GCATTGGCAG ACAGAGTCTT    4080

TACCACTGAG CCACCAGGGA AGCCCTGTGC ACTCACATTC TTGACCACAT ATATACCAAG    4140

ACACAGCTGT CCAGAGGGGT GGCGCAGGAC ACCCTAGCCT TAGGATACCC CCATCTTGCC    4200

TGCAGGGTAA GCTCTACCGC ACCAAACACA CTGTGATGAC CATGGGCTCA GACTTCCAGT    4260

ACGAGAATGC CAACACGTGG TTCAAAAATC TTGACAAGCT CATCCAGTTG GTCAATGCCC    4320
```

```
AGGTGAGTGT GCCTSCCCGT GGGMACTKGT WTTKGTWTCC CAGGGYTTKG GGTCACATAC      4380
ATTATCTATA GGTGCTRCCT TAGTTTTCTA TACTTAATAA GCTACCACAA ACTTAGTGGC      4440
TTAAAACAAT AGCAAGGATA TTACCTTACA GTTCTGTAGG TCACAAGTCT GACATGGGTC      4500
TCACTGGGCT AAAATCAAGA TGTTAGCAGG GCTGTGTTCT NCTGGAAGCT CTAGGGAAA       4560
GTCTCCTTGG CTCATCCAGC TTCATTANTA NTCCCTNCCC NAGAATGTCA TATTTCAATT      4620
CTCCATNCAA GTTTTAAGTA ATAAAATTGG AATATTGAAA GTTTAGTAAA ATCTCAGGTT      4680
TATTCTTGCA TCCCTCAATT TCTCTCCAGG CCAGGCTGGT AATTAGCTTG GNCCAATGTT      4740
CATTTTCACA CTTAGCCGTT GGTTTGTACT TAAACTGTGT ATTTAAAAAA AGAGAGAAAC      4800
TTTGNACCAA CCGGGTGCAT GAATGTGTGT GCCTGTGTTT GTGTGCATGT GCACACCTGT      4860
GGGCCCGCCC GGGAAGGGCT CCCGAGGGCT CACATAGGCA CACCTCCCCT CAGCAACGGG      4920
CCAACGGGAT CCGCGTCAAT GTTCTCTACT CTACCTCGGC CTGTTACCTC TGGGAGCTGA      4980
ACAAGGCCAA CCTCAGCTGG TATTTGGGGG GACTGGGGAG CCTCGGGGGG TTGGCATGCC      5040
CTGTGGGTCG TGGCCCTGCC CCCAATGTCT CTGCTGCTGC AGGTCAGTGA AAAAGGATGA      5100
CTTCTTCCCC TATGCTGATG GCCCCTACAT GTTCTGGACC GGTTACTTTT CCAGCCGGCC      5160
TGCCCTCAAA CGCTACGAGC GTCTCAGCTA CAATTTCCTG CAGGTAGGTG GACGCCAGGC      5220
TCCAGGGGCT GGCCCAGGGG TCCTGACAGG ACTGGTGCCC CAACATACCA CCTGCTCCAC      5280
AGGTGTGCAA CCAGCTGGAG GCGCTGGCGG GTCCGGCAGC CAACGTGGGA CCCTATGGCT      5340
CCGGGGACAG TGCACCCCTC AGTAGGTGTC GGCGGGCGAG GGGACAGCGG GGTGGGACTG      5400
AAGCTGGACT CCAGACTTCT ACTGTCCCTT TCTTAAAGCC TTTAAGAACC CAGCCTGCCA      5460
GACTTTTCGC ATGTCCTTGG GGTCTGGGCC GAGAGTCCTG CGGAGACCTC ACTTAGGCTA      5520
CACCGTCTGG CTACAGATGA GGCGATGGCC GTGCTCCAGC ACCATGATGC AGTCAGTGGT      5580
ACCTCCCGGC AGCACGTGGC TAACGACTAT GCCCGCCAAC TTTCAGAAGG CTGGAGGCCT      5640
TGCGAGGTGT GAGGGTGGGG CCTGGGGGAG GCGGAGACAG GAAGGGACTG GACCTGGACA      5700
CGGGGGCCGG AAGGTGGTGG GGGGCGGTGG GTGGTGGGGG CGGGGGTGGG GTCGGACTTA      5760
GGAAGGGGCG TGGTCGAAAA ACAGCCCGCC AGAAGGGCTC GTGGGCGGG GCTTGTGAAA       5820
GGAGGGACGG AGAGAGGCAG GGGCGGGGCT GAGAGCGGGA TCGCGAGGAG ACCGGCAGGG      5880
GCGTCCAGAG TGGAACTTTT GCTTTACACG CCTCCCCAGG TTCTCATGAG CAATGCGCTG      5940
GCGCATCTCA GCGGCTTAAA GGAGGACTTC GCCTTTTGTC GCAAGCTCAA CATCAGCATT      6000
TGTCCACTCA CGCAGACAGC AGAGAGAGTG AGCCGGCCTG GAGCGGGAGA GGCGGGGCTG      6060
GGGGCAGGTC CCGTGGGTGG TGGGTGGAAC GAGAACCAGA GAAACCTCTG GCCCAGTGA       6120
AAAGGAGGAG GGGCTGATGG GCTCAGCTGG TTACTGAGCA CTCTGGGCA AGATATTTGA       6180
GGGCTCAGTG AAGCTGGGGC AGGACGGGGA CCAATGCACC ACTTGGAGGC TTGACTCACC      6240
CAGGGACGTT GCTGCATACG TGGGTGGGTT TGCAGAAGGC CTGTTGTGAC CTGTGTCGGC      6300
TCTGACCATC CCACCCCAGT TCCAGGTGAT CGTTTATAAC CCCCTGGGGC GGAAAGTGGA      6360
CTGGATGGTG CGGCTGCCTG TCAGCAAACA CGTTTACCTC GTGAAGGACC CCGGTGGCAA      6420
AATTGTGCCC AGCGATGTTA ACCCATTTCC ACAAAATATC CCNCCCTGTG TGCCCACTTT      6480
AATAATACCA CCCCCTTGAA ACCCCCCTCA TGGCATTCTC CTTACCCATG ANATTCTAAA      6540
TAATTTTCCC TTCTGCTCCT TTAAATCATA ACCCCCTTGG GAACATTCCT GCCCCTCGCC      6600
TATGAGTATC TCCCCCTTGT TAATATCTCC CTGTGAAAAA ATTTCCTGTT TATGAATATT      6660
CTCCTCATCC TGAGGACCTC TCCCTCCTAA CCACTTCCTC CCCCCAGAAT CTGTTTTTCC      6720
```

| | | | | | |
|---|---|---|---|---|---|
| CTCCTTCCCC | TGTCTCAAGA | GTCTCTTCCC | ACGCTTAACT | CCCTCACTTC | TCCCACTTCC | 6780 |
| TACGGTACGT | CCACCCTTCT | GGTAGATTTC | CCACCTTCTG | AATCTTGGAA | TCTGTTTCTC | 6840 |
| TTTTTTTGGC | CATGCAGCTG | GCAAGATCTT | AGTTCCCCCA | CCAGGGGTCA | AACTNGTGTC | 6900 |
| CCCTGCAGTG | GATGTGGAGT | CTAACCACTG | GACTGCCAGG | GAATTCCCTC | TTTGCCATCT | 6960 |
| TTAACTCAGC | ATTTCTGACA | CTCCCACCCT | CTCTGCCCAA | CACCTAAATT | TCTTTTCCCC | 7020 |
| ATCTGGCAGG | TGTGACTCCT | TGCCCTCCTC | AAGTTTGACC | CCTTCCTGTT | TGTGTGGTGT | 7080 |
| GGCTTCATGC | ATGTCCTCCC | AGCTTCTTGA | CTTGGTTTCT | TCCTCCCTTA | CCTGAGGTGG | 7140 |
| TGACCATTCC | CAGTTCAGAC | AGTCAGGAGC | TGCTTTTCTC | AGCCTTAGTG | CCTGCCGTGG | 7200 |
| GCTTCAGCAT | CTACTCAGTC | TCCCAGATGC | CTAACCAAAG | ACCCCAGAAG | TCCTGGTCCC | 7260 |
| GTGACTTGGT | CATCCAGAAT | GAGGTGAGAC | CCTACTCAGA | CCCCCTTCCA | TTTCTGGGTG | 7320 |
| ATAGTTTTGA | GATGTGGCAG | TAAGCCACAT | GGACTGTGGG | TGAGTGGGCG | TGAAGTTTAT | 7380 |
| GGTCTTGTGT | CATCAGTCCT | CCACTGTATG | TTCTCAGTGT | CCTCTCTTGG | GGCTCTTATG | 7440 |
| TCACCCTTGG | GTGACACTTG | ATAGAAATGT | CAGAGCTGAT | GGAGGTATGG | GTTTGNAAAT | 7500 |
| TCAGTGAGGT | GTGTCAGAGA | CGTGGAGGAG | GTAGCTGTGT | TGGTCATTTG | GGGGTAAGAG | 7560 |
| AGATCCAGTC | AGGCAGGGAG | CACCCTCAAG | TTGGNAGGGT | GTTGGGTTGT | TCAAAAGACA | 7620 |
| NTCAATTGTG | TTCTGTGGGT | CCCTCNTTCA | ATTTCACCAA | ANAANCCTGG | GTCCCCAANA | 7680 |
| AGATGGAGAA | GGNAAGGCCA | TGGGAAGTGG | GGAAGAAGTG | GTCAAGATTG | AGGATTAGGG | 7740 |
| AAGAAAATGG | ACCTGTAAGA | TTTCCTNCCA | GTGATGCACA | ATGAGAGAGA | GAGAGGAGGG | 7800 |
| AAGGGTGGGT | GGACCTTATT | TTCCCCACCA | GGGATTGAAC | ACTCTCCTTC | TACCATGCAA | 7860 |
| GCTGTGAGTC | TAAATCACCC | GTCTGCCAGG | GAATTCCCAC | TTTGCAGTCT | TTAATTCAGC | 7920 |
| ATTTCAGACA | TGCGATCCTT | CCTGCCCAAC | ACCAGTGTTT | GCTCCTGATC | CCTGGGAAGA | 7980 |
| ACCATTGGTT | GAAGTGATGG | TCATTAATGT | CTGTCCACCC | TTTTACTCCC | CAGTACCTCC | 8040 |
| GGGCTAGGTT | TGACCCTAAC | ACAGGGCTCT | TGATGGAGTT | GGAGAACCTG | GAGCAGAATC | 8100 |
| TCTTGCTGCC | TGTTCGCCAA | GCCTTCTACT | GGTGAGAGAG | GACCACCAGG | TCAGGGGGTG | 8160 |
| GGGTGTGTGA | ACAGAGCTGA | GGTCCCTTGT | CTGACTCTCA | CCTGCCCTGG | CCCTAGGTAC | 8220 |
| AACGCCAGTA | CAGGTAACAA | CCTAAGCTCC | CAGGCCTCCG | GTGCCTACAT | CTTCAGACCC | 8280 |
| AACCAGAACA | AACCACTGTT | CGTGAGCCAC | TGGGCTCAGA | CCCACCTTGT | GAAGGTCAGG | 8340 |
| GGGCTGAGAG | TGGNNACTTG | GGGAANGGGN | GTNNAGGNTG | GGGTGNATGT | GGNGCGTGAT | 8400 |
| GTGCCTTGTG | AGGGGTGGTG | GGGAGAATTT | ACATCTCCAA | TAGATAAGAA | GGCTAAGACC | 8460 |
| AGAGGGAAT | ACTTGAGGAT | TTTCACACAG | GGTTGATAAT | CACAGCTGGT | TGTATGACAG | 8520 |
| TTACACATGG | AGGCCCATAG | AAAGGCATTT | CACATCTGTC | GTGGGATCA | GGAGTGTACT | 8580 |
| TAGCTTTGGA | AATTGGTGGG | TAGGCTTGTT | CCCATTTGGN | CCCTGAATGC | ACAGAGTCAA | 8640 |
| GTGTAACTTG | CCTGAAAATT | TCAATAGGGA | TCTTCGATAG | GAAGCCCCAN | AATTTCCAAA | 8700 |
| AACCCTGGAA | AGGACCATGG | CAAANGCANN | GGTTNAAANA | TAAAANCNCT | TGACCACTAA | 8760 |
| CACAAATCTG | GCACCAAGAT | TNATCCACAC | CCCAAAAACT | TANTTGCCAT | TGCTTGAGGA | 8820 |
| AAAAATCANT | TNATGTTTTG | TTGCCAAGCA | CCNAACCTAG | CAAGATAGGG | GAGGTGGGCT | 8880 |
| GGCCCCCGAA | CCTATTAAGT | GGGGTTGACC | CTGACGTAGG | CCTTTGTGAT | CTTCACANCT | 8940 |
| GGGGTGGACA | TTTGCAGGGC | TCACCTTTGC | TCAGGTGCAC | GCTTACACCT | GCCCCCACTC | 9000 |
| CCGTGTGCCC | ACAGGCGTCC | TTGGTGCAGG | AAGTACACCA | GAACTTCTCA | GCCTGGTGTT | 9060 |
| CCCAGGTGGT | TCGCCTGTAT | CCCAGACAAC | GGCACCTGGA | GCTAGAGTGG | ACAGTGGGGC | 9120 |

```
CAATACCTGT GGGGTGAGCG GGGCTGGGGG CTGGGGGAAG GNCAAAGTGA GGTTAAAGTG      9180
AAGCTCACCA CCTTGCCATC CCATTGGGTA TAGAGACGGC TGGGGGAAGG AGGTCATCAG      9240
TCGCTTTGAC ACTGCATTGG CGACACGCGG ACTCTTCTAC ACTGCAGCA ATGGCCGGGA       9300
GATCCTGGAG AGGAGGTGGA GAGACTGGGG GCACCGAGGG GTGGTCTGTG GTGTGCTGGG      9360
GCCCAGGGCA GTGAGGGGGC ATCTGCTGAT CCTAATGACT GTGGGAGGGA GAGGATGAAG      9420
GAGGAGTGGG TGAGTGGGGG GAAGGGAACC AGACTCCAAG CCTGATCNAA TCCTAACCCC      9480
ACCCCAGGCG GAATTATAGA CCTACCTGGA AGCTGAACCA GACTGAACCC GTGGCTGGAA      9540
ATTACTATCC AGTCAACAGC CGCATTTACA TCACGGTACC CATCCCCCAC CCTGCTCCCC      9600
ACCTTTTCCT GACACCCCTT TACAGAGTGG ACTTCACCTG TTCTTGACAT CTCCCAACTG      9660
TCCTCAGCAG TCTCCACCAT CCCTGTGGGG CCTGCCTGGG AGCCGGGGCT GGCCAGCAGT      9720
GCAGCCCCTC ACTCACCCTT TACCCCTCAG GATGGGAACA TGCAGCTGAC TGTGCTCACT      9780
GACCGGTCCC AGGGGGGCAG TAGCCTGAGA GATGGCTCCT TGGAACTCAT GGTTAGTGGT      9840
CTGAGCCCCC ATCTAAGTCA GGGTCCTTCC ACCAGTTCCC TTCCTGGCCT CTACAGGACT      9900
TGAGGCAGTT TCTTTTGGTA GGTGCACCCT TGGTTGNGGT CCCGCTAAGC TGAACCTCCA      9960
TCCTCTTGTG AGAAATCANT CCGGGTTTTT TCAATCCCTA CCAAATTCCG TTCAGGCCTG     10020
ATTACCTATG ACCCTACCCA AACTTCCGCT CCAGGCCCTG AATTACCCTA TGCACGCCCG     10080
CAATAGAACC TTACCGCCGT CTTCCCTAAN CCGTTNTTAG GNCGGAACCC CACATTTACT     10140
GGGGAACCCT TACGTTCCCT TCGTCGTCAA CCGTTTCCCC CAANAATTTT TTTTTCCCTT     10200
GAAATCCCCA CGTACTTTCA CCCAGTTTCC GGCCCAGAAA TTGGCTACAG GAACCCTCAC     10260
TCTTGGCCAC TCTCCCCGCA GGTCCACCGA AGGCTGCTGA AGGACGATGC ACGCGGAGTT     10320
GGGGAGCCGC TGAACAAGGA GGGGTCGGGG CTTTGGGTGC GAGGACGTCA CCTCGTGCTG     10380
TTGGATAAGA AGGAGACTGC GGCCGCCAGG CACCGGTTAC AGGCGGAGAT GGAGGTCCTG     10440
GCCCCGCAGG TGGTGCTGGC TCAAGGTGGC GGCGCGCGGT ATCGCCTCGA GAAAGCCCCA     10500
CGCACGCAGG TGANGAGGCN CGGCAGAAAG AGGACCCAAN GAACGCCTGC NGAGNGAGGG     10560
GCGGAGTTGA GGGCNGGTTN TCCTAGGTAN AACTGAGNGC CACCTCGGCT TGNGGTTGAC     10620
CAGGCCTCCT GATCNGGGTT GAGCNCNCCC TTCTGAATTG TATCACCCCC TCCTGTANCG     10680
TCTCANCCCC GCCCCTCCCG GCTCAGCCCC GCCCCGCTCT TTCCCTCAGT TCTCTGGGCT     10740
CCGCCGCGAG CTGCCACCCT CGGTACGTCT GCTCACATTG GCCCGCTGGG GCCCGGAGAC     10800
ACTGCTGCTG CGCTTAGAGC ACCAGTTCGC CGTAGGGAG GACTCGGGCC GGAACTTGAG      10860
CTCCCCGGTG ACCCTGGACT TGACGGTGAG GATAGAGATG GAAAGGAGAC TGGGGAGAGG     10920
AGGGAGGGA AACCCCGCTT NGTNCCAACG CATCCGGGCC CCTTCACTGC CCGCAGAACT      10980
TGTTTTCCGC CTTCACCATC ACCAACCTGC GGGAGACCAC GCTGGCGGCC AACCAGCTCC     11040
TGGCCTACGC CTCCAGGCTC CAGTGGACGA CGGACACGGG TAGGAGCCTG CCCGGAGCGG     11100
GGTGGCGGCC GGGGTCCGG NGAGGGGGC GGCGGNTCAG TGTGGGAGGT GCGGGAATGT       11160
TGACCCGGTC CAGGTATAGA GCTTGGAGGG TCGGAGTAAG TCGGTGTTCA GATTTAGGTT     11220
AGGGGTTTAA GGGAGTGATG TGGCTTGACA GTCCTTGAGG GTGGGACTTG TGGGTGTGAG     11280
GACAGTGCCC AGACACTGGG GAGAGATTTG AGCATCTGGG GGTGGTATCT AGGCTCTGGC     11340
AAACAGTTGA AGGGTCTGGG AGTGAGGNCC TGGGGAAAGA TTTAAANCGG TATGTCTGTG     11400
TTCAGGGGAG GNCGCACAGA GGATGTTAAG NCGGAGGAAG TCTGCATCCN TCACTTCTCC     11460
CCTCCACCTC NCCAGGCCCC ACACCCCATC CTTCTCCTTC CCGTCCGGTG TCCGCCACCA     11520
```

```
TCACGCTGCA GCCCATGGAA ATCCGTACCT TCTTGGCTTC GGTCCAATGG GAAGAGGACG    11580

GCTAGACCCA CTGGATACAA GACTACCGGC TCCGAGCCTG AGTTCTCTCT CCGGGGGCGG    11640

AGCCAACTCT CCCCCTTGTT GCTCTTACTA CCACCAATGA AAGCCATTAA AATGTCACTA    11700

CCG                                                                  11703
```

(2) INFORMATION FOR SEQ ID NO:4:

(i) SEQUENCE CHARACTERISTICS:
        (A) LENGTH: 296 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

```
CGCTGGACAC CCTAGCCTTA GGATACCCCC GTCTTGCCTG CAGGGTAAGC TCTACCGCAC      60

CAAACACACT GTGATGACCA TGGGCTCAGA CTTCCAGTAC GAGAATGCCA ACACGTGGTT     120

CAAAAATCTT GACAAGCTCA TCCAGTTGGT CAATGCCCAG GTGAGTGTGC CTCCCCGTGG     180

GCACTTGTAT TTGTATCCCA GGGCTTTGGG TCACATACAT TATCTATAGG TGCTGCCTTA     240

GTTTTCTATA CCTTAATAAG CTACCACAAA CTTAGTGGCT TAAAACAATA GCAAGG        296
```

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: NO (xi) SEQUENCE DESCRIPTION: SEQ ID NO:5:

```
CGCTGGACAC CCTAGCCTTA GGA                                             23
```

(2) INFORMATION FOR SEQ ID NO:6:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: YES (xi) SEQUENCE DESCRIPTION: SEQ ID NO:6:

```
CCTTGCTATT GTTTTAAGCC TCTAAGTTTG TGGT                                 34
```

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: YES (xi) SEQUENCE DESCRIPTION: SEQ ID NO:7:

CGCAGGACAC CCTAGCCTTA G                                              21

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: YES (xi) SEQUENCE DESCRIPTION: SEQ ID NO:8:

GGGCTGCGCG TGTCCTCCAC AA                                         22

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: YES (xi) SEQUENCE DESCRIPTION: SEQ ID NO:9:

CAGAAAATCG TGAGGGAACT GGTG                                     24

(2) INFORMATION FOR SEQ ID NO:10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: YES (xi) SEQUENCE DESCRIPTION: SEQ ID NO:10:

CGCAGGACAC CCTAGCCTTA GGA                                      23

(2) INFORMATION FOR SEQ ID NO:11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: YES (ix) FEATURE:
        (A) NAME/KEY: Base
        (B) LOCATION: 3
        (D) OTHER INFORMATION: /note= "N = inosine"

(ix) FEATURE:
        (A) NAME/KEY: Base
        (B) LOCATION: 9
        (D) OTHER INFORMATION: /note= "N = inosine"

(ix) FEATURE:
        (A) NAME/KEY: Base
        (B) LOCATION: 12
        (D) OTHER INFORMATION: /note= "N = inosine"

(ix) FEATURE:
        (A) NAME/KEY: Base
        (B) LOCATION: 15
        (D) OTHER INFORMATION: /note= "N = inosine"

(ix) FEATURE:
        (A) NAME/KEY: Base
        (B) LOCATION: 18
        (D) OTHER INFORMATION: /note= "N = inosine"

(ix) FEATURE:
        (A) NAME/KEY: Base
        (B) LOCATION: 21
        (D) OTHER INFORMATION: /note= "N = inosine"

(ix) FEATURE:
        (A) NAME/KEY: Base
        (B) LOCATION: 24
        (D) OTHER INFORMATION: /note= "N = inosine"

(ix) FEATURE:
        (A) NAME/KEY: Base
        (B) LOCATION: 27
        (D) OTHER INFORMATION: /note= "N = inosine"

(xi) SEQUENCE DESCRIPTION: SEQ ID NO:11:

ATNTACAANA CNGTNCCNAA NGTNAANCC                              29

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: NO (ix) FEATURE:
        (A) NAME/KEY: Base
        (B) LOCATION: 3
        (D) OTHER INFORMATION: /note= "N = inosine"

```
    (ix) FEATURE:
         (A) NAME/KEY: Base
         (B) LOCATION: 9
         (D) OTHER INFORMATION: /note= "N = inosine"

(ix) FEATURE:
         (A) NAME/KEY: Base
         (B) LOCATION: 12
         (D) OTHER INFORMATION: /note= "N = inosine"

(ix) FEATURE:
         (A) NAME/KEY: Base
         (B) LOCATION: 18
         (D) OTHER INFORMATION: /note= "N = inosine"

(ix) FEATURE:
         (A) NAME/KEY: Base
         (B) LOCATION: 21
         (D) OTHER INFORMATION: /note= "N = inosine"

(ix) FEATURE:
         (A) NAME/KEY: Base
         (B) LOCATION: 24
         (D) OTHER INFORMATION: /note= "N = inosine"

(xi) SEQUENCE DESCRIPTION: SEQ ID NO:12:

ACNGCCATNG CNTCATTNAG NGGNGC                                              26

(2) INFORMATION FOR SEQ ID NO:13:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "oligonucleotide"

(iii) HYPOTHETICAL: NO (iv) ANTI-SENSE: NO (xi) SEQUENCE DESCRIPTION: SEQ ID NO:13:

AGAGAGGCGG GAGCGGTGG                                                     19

(2) INFORMATION FOR SEQ ID NO:14:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "oligonucleotide"

(iii) HYPOTHETICAL: NO (iv) ANTI-SENSE: YES (xi) SEQUENCE DESCRIPTION: SEQ ID NO:14:

CAGAAAATCG TGAGGGAACT GGTG                                               24

(2) INFORMATION FOR SEQ ID NO:15:

(i) SEQUENCE CHARACTERISTICS:
         (A) LENGTH: 20 base pairs
         (B) TYPE: nucleic acid
         (C) STRANDEDNESS: single
         (D) TOPOLOGY: linear
```

(ii) MOLECULE TYPE: other nucleic acid
            (A) DESCRIPTION: /desc = "oligonucleotide"

(iii) HYPOTHETICAL: NO (iv) ANTI-SENSE: YES (xi) SEQUENCE DESCRIPTION: SEQ ID NO:15:

GTGGCGGCGG CGGCTGCAGA                                                           20

(2) INFORMATION FOR SEQ ID NO:16:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: NO (xi) SEQUENCE DESCRIPTION: SEQ ID NO:16:

GGGCTACGCG TGTCCTCCAC AA                                                        22

(2) INFORMATION FOR SEQ ID NO:17:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: YES (xi) SEQUENCE DESCRIPTION: SEQ ID NO:17:

CCACCGCTCC CGCCTCTCT                                                            19

(2) INFORMATION FOR SEQ ID NO:18:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: YES (xi) SEQUENCE DESCRIPTION: SEQ ID NO:18:

ACTGACAGAG TGAGTGTGTG                                                           20

(2) INFORMATION FOR SEQ ID NO:19:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: NO (xi) SEQUENCE DESCRIPTION: SEQ ID NO:19:

TCATCATGTG TGTGAGGCA                                                    19

(2) INFORMATION FOR SEQ ID NO:20:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: YES (xi) SEQUENCE DESCRIPTION: SEQ ID NO:20:

TCTCTTCCTT GCTGGCGAAT CC                                                22

(2) INFORMATION FOR SEQ ID NO:21:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: YES (xi) SEQUENCE DESCRIPTION: SEQ ID NO:21:

CAGAAAATCG TGAGGGAACT GGTG                                              24

(2) INFORMATION FOR SEQ ID NO:22:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: YES (xi) SEQUENCE DESCRIPTION: SEQ ID NO:22:

GGAACAGGAC GCCTAGAGT                                                    19

(2) INFORMATION FOR SEQ ID NO:23:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: NO (xi) SEQUENCE DESCRIPTION: SEQ ID NO:23:

CGCAGTCTGA GTGTCATCTG G                                                    21

(2) INFORMATION FOR SEQ ID NO:24:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: YES (xi) SEQUENCE DESCRIPTION: SEQ ID NO:24:

AAGACGCTGC AGATGGAGCA GG                                                   22

(2) INFORMATION FOR SEQ ID NO:25:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: NO (xi) SEQUENCE DESCRIPTION: SEQ ID NO:25:

TCCACTCTAC CACCTTACTG                                                      20

(2) INFORMATION FOR SEQ ID NO:26:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: NO (xi) SEQUENCE DESCRIPTION: SEQ ID NO:26:

GGGCTACGCG TGTCCTCCAC AA                                                   22

(2) INFORMATION FOR SEQ ID NO:27:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
    (A) DESCRIPTION: /desc = "oligonucleotide"

(iii) HYPOTHETICAL: NO (iv) ANTI-SENSE: YES (xi) SEQUENCE DESCRIPTION: SEQ ID NO:27:

TTGTGGAGGA CACGCGTAGC CC                                              22

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: NO (xi) SEQUENCE DESCRIPTION: SEQ ID NO:28:

GAACCACGTG TTGGCATTCT                                                  20

(2) INFORMATION FOR SEQ ID NO:29:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: NO (xi) SEQUENCE DESCRIPTION: SEQ ID NO:29:

CCTTGCTATT GTTTTAAGCC TCTAAGTTTG                                       30

(2) INFORMATION FOR SEQ ID NO:30:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: YES (xi) SEQUENCE DESCRIPTION: SEQ ID NO:30:

CAAGCTCATC CAGTTGGTCA ATG                                              23

(2) INFORMATION FOR SEQ ID NO:31:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: YES (xi) SEQUENCE DESCRIPTION: SEQ ID NO:31:

TCCGCGTCAA TGTTCTCTAC TC                                                22

(2) INFORMATION FOR SEQ ID NO:32:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: NO (xi) SEQUENCE DESCRIPTION: SEQ ID NO:32:

TTCACTGACC AGCTGAGGTT GGC                                               23

(2) INFORMATION FOR SEQ ID NO:33:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: NO (xi) SEQUENCE DESCRIPTION: SEQ ID NO:33:

GAGGTACCAC TGACTGCATC A                                                 21

(2) INFORMATION FOR SEQ ID NO:34:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: YES (xi) SEQUENCE DESCRIPTION: SEQ ID NO:34:

CATGATGCAG TCAGTGGTAC CT                                                22

(2) INFORMATION FOR SEQ ID NO:35:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: YES (xi) SEQUENCE DESCRIPTION: SEQ ID NO:35:

TTGTCGCAAG CTCAACATCA G                                                  21

(2) INFORMATION FOR SEQ ID NO:36:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: NO (xi) SEQUENCE DESCRIPTION: SEQ ID NO:36:

TCTCTGCTGT CTGCGTGAGT G                                                  21

(2) INFORMATION FOR SEQ ID NO:37:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: YES (xi) SEQUENCE DESCRIPTION: SEQ ID NO:37:

TCAGGAGCTG CTTTTCTCAG CCT                                                23

(2) INFORMATION FOR SEQ ID NO:38:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: NO (xi) SEQUENCE DESCRIPTION: SEQ ID NO:38:

GGAGACTGAG TAGATGCTGA                                                    20

(2) INFORMATION FOR SEQ ID NO:39:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: NO (xi) SEQUENCE DESCRIPTION: SEQ ID NO:39:

TAGAAGGCTT GGCGAACAGG CAGC                                          24

(2) INFORMATION FOR SEQ ID NO:40:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: YES (xi) SEQUENCE DESCRIPTION: SEQ ID NO:40:

GGTGCCTACA TCTTCAGAC                                                19

(2) INFORMATION FOR SEQ ID NO:41:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: NO (xi) SEQUENCE DESCRIPTION: SEQ ID NO:41:

CCTCACAAGG CACATCACG                                                19

(2) INFORMATION FOR SEQ ID NO:42:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: YES (xi) SEQUENCE DESCRIPTION: SEQ ID NO:42:

GCTCAGGTGC ACGCTTACA                                                19

(2) INFORMATION FOR SEQ ID NO:43:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: YES (xi) SEQUENCE DESCRIPTION: SEQ ID NO:43:

CGGCCATTGC TGTCAGTGAG AA                                               22

(2) INFORMATION FOR SEQ ID NO:44:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: YES (xi) SEQUENCE DESCRIPTION: SEQ ID NO:44:

AAATTACTAT CCAGTCAACA                                                  20

(2) INFORMATION FOR SEQ ID NO:45:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: NO (xi) SEQUENCE DESCRIPTION: SEQ ID NO:45:

GGAGATGTCA AGAACAGGTG                                                  20

(2) INFORMATION FOR SEQ ID NO:46:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: YES (xi) SEQUENCE DESCRIPTION: SEQ ID NO:46:

CAGCACGAGG TGACGTCCTC GCA                                              23

(2) INFORMATION FOR SEQ ID NO:47:

(i) SEQUENCE CHARACTERISTICS:
        (A) LENGTH: 21 base pairs
        (B) TYPE: nucleic acid
        (C) STRANDEDNESS: single
        (D) TOPOLOGY: linear

```
    (ii) MOLECULE TYPE: other nucleic acid
         (A) DESCRIPTION: /desc = "oligonucleotide"

(iii) HYPOTHETICAL: NO (iv) ANTI-SENSE: YES (xi) SEQUENCE DESCRIPTION: SEQ ID NO:47:

GGAGGTCCTG GCCCCGCAGG T                                              21

(2) INFORMATION FOR SEQ ID NO:48:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "oligonucleotide"

(iii) HYPOTHETICAL: NO (iv) ANTI-SENSE: YES (xi) SEQUENCE DESCRIPTION: SEQ ID NO:48:

GACGGTGAGG ATAGAGATGG A                                              21

(2) INFORMATION FOR SEQ ID NO:49:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "oligonucleotide"

(iii) HYPOTHETICAL: NO (iv) ANTI-SENSE: NO (xi) SEQUENCE DESCRIPTION: SEQ ID NO:49:

GGAGCTGGTT GGCCGCCAGC GT                                             22

(2) INFORMATION FOR SEQ ID NO:50:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "oligonucleotide"

(iii) HYPOTHETICAL: NO (iv) ANTI-SENSE: YES (xi) SEQUENCE DESCRIPTION: SEQ ID NO:50:

CGCCTCCAGG CTCCAGTGGA C                                              21

(2) INFORMATION FOR SEQ ID NO:51:

(i) SEQUENCE CHARACTERISTICS:
         (A) LENGTH: 24 base pairs
         (B) TYPE: nucleic acid
         (C) STRANDEDNESS: single
         (D) TOPOLOGY: linear
```

```
        (ii) MOLECULE TYPE: other nucleic acid
             (A) DESCRIPTION: /desc = "oligonucleotide"

(iii) HYPOTHETICAL: NO (iv) ANTI-SENSE: NO (xi) SEQUENCE DESCRIPTION: SEQ ID NO:51:

TCTGAACACC GACTTACTCC GACC                                              24

(2) INFORMATION FOR SEQ ID NO:52:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "oligonucleotide"

(iii) HYPOTHETICAL: NO (iv) ANTI-SENSE: NO (xi) SEQUENCE DESCRIPTION: SEQ ID NO:52:

CCTGAACACA GACATACC                                                     18

(2) INFORMATION FOR SEQ ID NO:53:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "oligonucleotide"

(iii) HYPOTHETICAL: NO (iv) ANTI-SENSE: NO (xi) SEQUENCE DESCRIPTION: SEQ ID NO:53:

GGCTTTCATT GGTGGTAGTA AGAGCA                                            26

(2) INFORMATION FOR SEQ ID NO:54:

(i) SEQUENCE CHARACTERISTICS:
             (A) LENGTH: 10 amino acids
             (B) TYPE: amino acid
             (C) STRANDEDNESS: Not Relevant
             (D) TOPOLOGY: Not Relevant (ii) MOLECULE TYPE: peptide (iii) HYPOTHETICAL: not relevant (iv) ANTI-SENSE: not relevant (v) FRAGMENT TYPE: internal (xi) SEQUENCE DESCRIPTION: SEQ ID NO:54:

Xaa Xaa Xaa Val Asn Xaa Xaa Tyr Ser Thr
1               5                   10

(2) INFORMATION FOR SEQ ID NO:55:

(i) SEQUENCE CHARACTERISTICS:
             (A) LENGTH: 24 amino acids
             (B) TYPE: amino acid
```

(C) STRANDEDNESS: Not Relevant
        (D) TOPOLOGY: Not Relevant (ii) MOLECULE TYPE: peptide (iii) HYPOTHETICAL: not relevant (iv) ANTI-SENSE: not relevant (v) FRAGMENT TYPE: internal (xi) SEQUENCE DESCRIPTION: SEQ ID NO:55:

Xaa Ile Tyr Lys Ala Val Leu Tyr Ser Thr Pro Ala Val Val Thr Pro
1               5                   10                  15
Pro Lys Val Lys Met Met Asn Ala
            20

(2) INFORMATION FOR SEQ ID NO:56:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: not relevant (iv) ANTI-SENSE: not relevant (v) FRAGMENT TYPE: internal (xi) SEQUENCE DESCRIPTION: SEQ ID NO:56:

Xaa Leu Leu Pro Val Val Gln Ala Phe Tyr
1               5                   10

(2) INFORMATION FOR SEQ ID NO:57:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: not relevant (iv) ANTI-SENSE: not relevant (v) FRAGMENT TYPE: internal (xi) SEQUENCE DESCRIPTION: SEQ ID NO:57:

Xaa Xaa Tyr Lys Thr Xaa Pro Lys Val Lys Pro
1               5                   10

(2) INFORMATION FOR SEQ ID NO:58:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: not relevant (iv) ANTI-SENSE: not relevant (v) FRAGMENT TYPE: internal (xi) SEQUENCE DESCRIPTION: SEQ ID NO:58:

Xaa Gly Xaa Ser Ala Pro Leu Asn Glu Ala Met Ala Val Leu Gln Asp
1               5                   10                  15

(2) INFORMATION FOR SEQ ID NO:59:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:59:

GGGATACAAG GTGAGCGCGG        20

(2) INFORMATION FOR SEQ ID NO:60:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:60:

CCCTGTGCAG ACATGCCCGA        20

(2) INFORMATION FOR SEQ ID NO:61:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:61:

TTCTATGGCA GTGAGTAGAG        20

(2) INFORMATION FOR SEQ ID NO:62:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:62:

GTGCCCACAG TCTACAATAA                                                   20

(2) INFORMATION FOR SEQ ID NO:63:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:63:

GTGCGCCAGG GTGAGCCTCC                                                   20

(2) INFORMATION FOR SEQ ID NO:64:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:64:

CCCGGCACAG GACGCCTAGA                                                   20

(2) INFORMATION FOR SEQ ID NO:65:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:65:

GTTCGCGCAG GTTTTCAGAT                                                   20

(2) INFORMATION FOR SEQ ID NO:66:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:66:

CCANCTCCAG ATGGGTTTTG                                                   20

(2) INFORMATION FOR SEQ ID NO:67:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:67:

CTCTTCACCA GTAAGGTGGT                                        20

(2) INFORMATION FOR SEQ ID NO:68:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:68:

TGGTCCGCAG GTGTGCTCCC                                        20

(2) INFORMATION FOR SEQ ID NO:69:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:69:

CACTGACCAG GTAACCGGGT                                        20

(2) INFORMATION FOR SEQ ID NO:70:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:70:

TTGCCTGCAG GGTAAGCTCT                                        20

```
(2) INFORMATION FOR SEQ ID NO:71:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:71:

CAATGCCCAG GTGAGTGTGC                                             20

(2) INFORMATION FOR SEQ ID NO:72:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:72:

CTCCCCTCAG CAACGGGCCA                                             20

(2) INFORMATION FOR SEQ ID NO:73:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:73:

ACCTCAGCTG GTATTTGGGG                                             20

(2) INFORMATION FOR SEQ ID NO:74:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:74:

GCTGCTGCAG GTCAGTGAAA                                             20
```

-continued (2) INFORMATION FOR SEQ ID NO:75:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:75:

TTTCCTGCAG GTAGGTGGAC                                                      20

(2) INFORMATION FOR SEQ ID NO:76:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:76:

TGCTCCACAG GTGTGCAACC                                                      20

(2) INFORMATION FOR SEQ ID NO:77:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:77:

GCACCCCTCA GTAGGTGTCG                                                      20

(2) INFORMATION FOR SEQ ID NO:78:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:78:

CTGGCTACAG ATGAGGCGAT                                                      20

(2) INFORMATION FOR SEQ ID NO:79:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:79:

GCCTTGCGAG GTGTGAGGGT                                                    20

(2) INFORMATION FOR SEQ ID NO:80:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:80:

GCCTCCCCAG GTTCTCATGA                                                    20

(2) INFORMATION FOR SEQ ID NO:81:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:81:

AGCAGAGAGA GTGAGCCGGC                                                    20

(2) INFORMATION FOR SEQ ID NO:82:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:82:

CCCACCCCAG TTCCAGGTGA                                                    20

(2) INFORMATION FOR SEQ ID NO:83:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:83:

GCCCAGCGAT GTTAACCCAT                                                20

(2) INFORMATION FOR SEQ ID NO:84:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:84:

CTTACCTGAG GTGGTGACCA                                                20

(2) INFORMATION FOR SEQ ID NO:85:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:85:

CCAGAATGAG GTGAGACCCT                                                20

(2) INFORMATION FOR SEQ ID NO:86:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:86:

TACTCCCCAG TACCTCCGGG                                                20

(2) INFORMATION FOR SEQ ID NO:87:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:87:

CCTTCTACTG GTGAGAGAGG                                      20

(2) INFORMATION FOR SEQ ID NO:88:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:88:

CTGGCCCTAG GTACAACGCC                                      20

(2) INFORMATION FOR SEQ ID NO:89:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:89:

CCTTGTGAAG GTCAGGGGGC                                      20

(2) INFORMATION FOR SEQ ID NO:90:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:90:

GTGCCCACAG GCGTCCTTGG                                      20

(2) INFORMATION FOR SEQ ID NO:91:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:91:

TACCTGTGGG GTGAGCGGGG                                                  20

(2) INFORMATION FOR SEQ ID NO:92:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:92:

TTGGNTATAG AGACGGCTGG                                                  20

(2) INFORMATION FOR SEQ ID NO:93:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:93:

TGGAGAGGAG GTGGAGAGAC                                                  20

(2) INFORMATION FOR SEQ ID NO:94:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:94:

CCCACCCCAG GCGGAATTAT                                                  20

(2) INFORMATION FOR SEQ ID NO:95:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:95:

TTACATCACG GTACCCATCC     20

(2) INFORMATION FOR SEQ ID NO:96:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:96:

TACCCCTCAG GATGGGAACA     20

(2) INFORMATION FOR SEQ ID NO:97:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:97:

GGAACTCATG GTTAGTGGTC     20

(2) INFORMATION FOR SEQ ID NO:98:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:98:

CTCCCCGCAG GTGCACCGAA     20

(2) INFORMATION FOR SEQ ID NO:99:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:99:

ACGCACGCAG GTGANGAGGC                                                20

(2) INFORMATION FOR SEQ ID NO:100:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:100:

TTTCCCTCAG TTCTCTGGGC                                                20

(2) INFORMATION FOR SEQ ID NO:101:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:101:

GGACTTGACG GTGAGGATAG                                                20

(2) INFORMATION FOR SEQ ID NO:102:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:102:

CTGCCCGCAG AACTTGTTTT                                                20

-continued (2) INFORMATION FOR SEQ ID NO:103:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:103:

ACGGACACGG GTAGGAGCCT                                                              20

(2) INFORMATION FOR SEQ ID NO:104:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:104:

ACCTCNCCAG GCCCCACACC                                                              20

GENETIC TEST FOR α-MANNOSIDOSIS

The present invention relates to α-mannosidosis and its detection, in particular the detection of bovine α-mannosidosis.

α-mannosidosis is an autosomal, recessively inherited lysosomal storage disorder that has been clinically well characterised (M. A. Chester et al., 1982, in Genetic Errors of Glycoprotein Metabolism pp 90–119, Springer Verlag, Berlin). It is a very common disease in cattle but has also been found in man and cat. Glycoproteins are normally degraded stepwise in the lysosome and one of the steps, namely the cleavage of α-linked mannose residues from the non-reducing end during the ordered degradation of N-linked glycoproteins is catalysed by the enzyme lysosomal α-mannosidase (EC 3.2.1.24). However, in α-mannosidosis, a deficiency of the enzyme α-mannosidase results in the accumulation of mannose rich oligosaccharides. As a result, the lysosomes increase in size and swell, which impairs cell functions.

In man, the disease is rare. The symptoms of α-mannosidosis include psychomotor retardation, ataxia, impaired hearing, vacuolized lymphocytes in the peripheral blood and skeletal changes. (Chester et al supra).

In cattle the disorder is much more common and results in mental retardation, skeletal changes, ataxia, a fine head tremor, aggressive behaviour and premature death. The disease has been reported among cattle in both Northern and Southern Hemispheres and in different breeds of cattle. Among cattle of the Angus breed there is a variation in phenotypic expression spanning from death within days to slowly progressing neurological deterioration that lasts for months (Healy et al., 1990, Res. Vet. Sci., 49: 82–84). Among other breeds of cattle such as Galloway, the symptoms can be more severe resulting in still birth or death within a few days after birth (Healy et al supra). As mentioned above, α-mannosidosis is widespread in cattle and consequently is of considerable economic importance.

Currently, no treatment of the disease is available and consequently, not only are diseased cattle lost with respect to meat production, but it is important to prevent spread of the disease in breeding programmes. There is therefore a need to detect cattle that have or are carriers of α-mannosidosis. A known method of detection has been to determine the enzyme activity of lysosomal α-mannosidase. It is generally decreased to 40% of normal activity among cattle carrying α-mannosidosis (ie. heterozygotes) and less than 10% in cattle exhibiting full α-mannosidosis (ie. homozygotes). However, activity levels may vary between individuals and it sometimes becomes difficult to distinguish normal cattle from heterozygous carriers. This severely limits the utility of the enzyme test in detecting carriers.

The enzyme activity assay requires withdrawal of a blood sample less than 24 hours before analysis is begun. The enzyme activity is determined in isolated granulocytes (Healy, 1981, Res. Vet. Sci., 30: 281–283) so it is first necessary to isolate and purify the white blood cells. The enzyme activity is determined using the calorimetric substance p-nitrophenyl alpha D-mannopyranoside at pH 3.7 or 4-methyl umbelliferyl alpha D-mannopyranoside. This enzymatic test is very sensitive, contamination of the cells can result in erroneous results and in some instances it might be difficult to distinguish between heterozygous and normal values of α-mannosidase activity.

The fact that only a short time can lapse between the taking of the sample from the animal and laboratory analysis means significant expense is incurred in ensuring speedy delivery to the laboratory and once at the laboratory samples have to be processed immediately, with the use of time consuming cell isolation techniques. The blood sample must usually be taken by a vet adding to the cost of the test. Thus, it will be seen that the disadvantages of the enzyme test are not inconsiderable and there remains a need for a straightforward and inexpensive text to detect cattle that have or are carriers of α-mannosidosis.

The nucleotide sequence of human lysosomal α-mannosidase has been determined (Nebes and Schmidt, 1994, Biochem. Biophys. Res. Comm., 200: 239–245) and a mutation causing α-mannosidosis in humans identified, namely a base transition results in a His to Leu replacement in a conserved region of the gene for α-mannosidase (Tollersrud et al., 1995, 10th ESGLD Workshop, Cambridge, England). However, in the case of cattle, full sequence information for the gene encoding bovine lysosomal α-mannosidase (LAMAN) gene is not available, and more significantly, a corresponding mutation in the gene encoding LAMAN has not up to now been known. Consequently no gene based test for the disease in cattle has up to now been available.

Mutations in the gene encoding bovine LAMAN which cause α-mannosidosis in cattle have now been elucidated, enabling and leading to the development of a genetic test for the disease.

Thus, in one aspect, the present invention provides a method for diagnosing or screening for bovine α-mannosidosis, comprising detecting, in nucleic acid samples from cattle, the presence or absence of α-mannosidosis-causing mutations in the gene encoding bovine LAMAN.

The present invention thus provides a method which not only enables the ready diagnosis of diseased cattle, but also permits cattle to be screened for the presence of the disease-causing allele of the LAMAN-encoding gene, enabling carriers to be detected and removed from breeding programmes. As used herein, the term "screening" thus includes detecting the presence of mutated LAMAN-encoding alleles in healthy cattle, ie. carriers, as well as in diseased animals. In this aspect, the invention can thus be seen to provide a genetic test for detecting the disease-causing α-mannosidase gene in cattle.

As mentioned above, our studies have shown that point mutations in the LAMAN gene can be identified which are associated with the α-mannosidase phenotype. Such α-mannosidosis-causing mutations are thus base transitions in the LAMAN-encoding gene, leading to amino acid substitutions in the encoded LAMAN protein.

In a further aspect, the present invention thus provides a method of detecting α-mannosidosis-causing mutations in cattle, comprising detecting the presence or absence of base transitions in the gene encoding bovine LAMAN, which are associated with disease.

As used herein the term "associated with disease" means that the base transitions result, as discussed above, in amino acid substitutions in the LAMAN protein which affect the functioning of the enzyme such that in homozygotes, α-mannosidosis is caused.

As will be described in more detail in the Examples below, in work leading to the present invention, bovine LAMAN has been purified and been found to be encoded by a single gene. A cDNA encoding the bovine LAMAN protein has been prepared and sequenced (SEQ ID No. 1) and is shown in FIG. 1, together with its amino acid translation in single letter code. Genomic sequencing studies of the bovine LAMAN-encoding gene have also been under-taken and a partial genomic sequence is shown in FIG. 2 (SEQ ID No. 3).

Such sequences represent further aspects of the invention. Thus, in a further aspect, the present invention can be seen to provide a nucleic acid molecule comprising all or a portion of a nucleotide sequence as shown in any one of FIG. 1 or 2 (SEQ. ID Nos. 1 or 3) or a sequence which is complementary thereto, or which is a degenerate or allelic variant thereof, or a substantially homologous sequence having at least 85%, preferably at least 90% sequence identity therewith.

A still further aspect of the invention provides the use of a nucleic acid molecular comprising a nucleotide sequence as shown in FIG. 1 or 2 or (SEQ ID Nos. 1 or 3) a sequence which is complementary thereto, or which is a degenerate or allelic variant thereof, or is a substantially homologous sequence having at least 85%, preferably at least 90% sequence identify therewith, or a part of any said sequence, in the detection of α-mannosidosis-causing mutation in the gene encoding bovine LAMAN.

RNA transcripts of the above-mentioned nucleotide sequences may also be used.

Sequencing of the bovine LAMAN cDNA was carried out by the use of PCR techniques on DNA extracted from a bovine cDNA library. Details, including the primers used, are given in the Examples below. cDNA from normal and affected cattle were compared by direct sequencing of PCR products and a number of different breeds were studied. This enabled us to determine that α-mannosidosis in different cattle breeds may be associated with different mutations, ie. different base transitions, at different positions in the bovine LAMAN gene, leading to different amino acid replacements or substitutions in the LAMAN protein. The present invention thus encompasses the detection of a range of different mutations ie. point mutations or base transitions in the bovine LAMAN gene, which may be associated with α-mannosidosis, and which may vary, both within breeds, and from breed to breed. Thus, for example, the breeds Angus, Murray Grey (which is a breed derived from Angus) and Galloway were studied, these representing breeds of economic importance and wide distribution.

In cDNA from the Angus breed of cattle, a single nucleotide substitution cytosine (C) for thymine (T), was identified that was predicted to result in the substitution of the amino acid leucine for phenylalanine. The particular phenylalanine residue is conserved between a number of different species indicating an important physiological function. It was found that the T to C substitution was conserved in both alleles of 3 Angus cattle affected by α-mannosidosis, in one of the alleles of 12 carriers of the disease and in no alleles of 58 normal Angus cattle. Similar results have been observed with Murray Grey and Red Angus cattle. Thus, we have found that the base transition ie. of the cDNA encoding bovine LAMAN, T to C at position 961 (T961C) of FIG. 1 (position 975 of SEQ ID No. 1), leading to an amino acid substitution of Phenylalanine (Phe) to Leucine (Leu) at amino acid position 321 is associated with the α-mannosidase-causing genotype in Angus and Angus-derived breeds of cattle, such as Murray Grey, Red Angus and Brangus.

In another breed of cattle, Galloway, comparison of the sequences of normal LAMAN cDNA and cDNA from a carrier of α-mannosidosis also revealed a base transition at a single position, but different from the position in Angus. In Galloway cattle there appears to be a G to A transition at position 662 of FIG. 1 (position 677 of SEQ ID No. 1), leading to an amino acid substitution of Arginine (Arg) to Histidine (His) at position 221. Only Arginine or Lysine appear at this position in the particular class of α-mannosidase, indicating that these closely related side chains are physiologically important in this position. The G to A transition was found in both alleles of 2 affected Galloway cattle, in one of the alleles of each of 7 carriers and in no alleles of 29 normal Galloway cattle. Thus, in the Galloway breed of cattle, the G to A transition at position 662 (G662A) of FIG. 1 (SEQ ID No. 1) appears to be primarily associated with α-mannosidosis.

Thus, in a particular aspect, according to the invention there is provided a DNA molecule which codes for bovine LAMAN as hereinbefore defined, wherein the nucleotide at position 961 of FIG. 1 (SEQ ID No. 1) is cytosine. Also provided, is a DNA molecule coding for bovine LAMAN, wherein the nucleotide at position 662 of FIG. 1 (SEQ ID No. 1) is adenine.

In a preferred embodiment, the present invention also provides methods of diagnosis or screening, and methods of detection as hereinbefore defined, wherein the base transitions T to C at position 961 of FIG. 1 (SEQ ID No. 1) (T961C) and/or G to A at position 662 of FIG. 1 (SEQ ID No. 1)(G662A) are detected.

Having identified mutations causing α-mannosidosis in cattle, straightforward gene based tests may be developed for identifying the mutant alleles, particularly in carriers which have one normal unmutated allele for the LAMAN gene. At their broadest, as mentioned above, such tests involve the detection of the aforementioned alleles. Such tests, which are exemplified in more detail below, have been developed and constitute further aspects of the present invention.

The present gene based detection methods which form aspects of the present invention have advantages over the earlier enzyme assays, as only very small amounts of starting material are required. For example, hair roots contain sufficient DNA for mutation detection studies. Other sources of DNA for the detection method include semen. Moreover, as DNA is relatively stable the samples may be sent via ordinary mail to the laboratories for testing and can be stored for several months below −20° C. without degradation of the DNA. The DNA based detection method is more reliable than the enzymatic test for detection of heterozygosity; the enzyme activity in carriers and normal cattle may overlap, whereas the frequency of mutated alleles in a heterozygous subject is strictly 50%. Those cattle homozygous for the mutated allele are likely to exhibit symptoms which can be observed by eye and it is therefore the detection of heterozygous carriers which is most important. Nucleic acid based detection methods also minimise the risk of contamination, for example from viruses which may be found in blood samples.

The methods of the invention may be carried out on any nucleic acid carrying or containing sample from cattle, including any such tissue or body fluid sample. Thus while samples such as blood, or blood derived samples may be used, the tests may conveniently be carried out as readily and easily obtainable samples such as semen, saliva or hair roots. The nucleic acid for analysis may be extracted from such samples using standard extraction or isolation techniques which are well known and widely described in the literature (see for example Sambrook et al., 1989, in Molecular Cloning: A Laboratory Manual, 2nd edition). The nucleic acid may be RNA or DNA, but conveniently will be DNA, and may be subjected to amplification using eg. any of the widely available in vitro amplification techniques.

Any method of detecting the disease-causing mutations ie. base transitions may be used according to the invention, and many suitable methods are described in the literature. Thus, for example, any method described in the literature for detecting known point mutations may be used.

A test which includes the amplification of a DNA fragment by PCR has been developed. Oligonucleotide primers that are complementary to DNA sequences upstream and downstream of the α-mannosidosis causing mutation are synthesised. These primers are used to amplify the DNA region that is located between them. Due to the amplification step, small amounts of starting material may be employed, for example, hair roots contain sufficient DNA for mutation detection studies.

As mentioned above, the mutation can be detected by a number of techniques known in the art which include DNA sequencing; cleavage of RNA-DNA or RNA-RNA hybrids at mutation sites using RNase; mis-match detection using heteroduplex analysis; detection of mutations by single-strand conformation polymorphism analysis; detection of mutations by denaturing gradient gel electrophoresis; chemical or enzymatic cleavage of heteroduplex DNA to identify mutations and detection of mutations by restriction fragment length polymorphism (RFLP).

In the case of the α-mannosidosis-causing mutations which have been identified according to the present invention, a single base is substituted in an allele which codes for the substantially inactive (ie. mutated) form of α-mannosidase. This base transition causes a change in the number of restriction sites in the gene, so the digest resulting from treatment with a particular restriction enzyme will vary between normal and mutated alleles. Thus for example, in the case of the Angus and Angus-related breeds the T 961 C substitution results in the creation of an extra site for the restriction enzyme Mnl I, which may be used to distinguish the normal and mutant alleles, since the mutant sequence will be cleaved at this site by Mnl I, whereas the normal sequence will not, resulting in a different restriction digestion pattern. FIG. 3 shows the different fragments that result when part of the α-mannosidase gene in Angus cattle is treated with the restriction enzyme Mnl I.

In the case of the Galloway breed, the G 662 A substitution results in the loss of a Bsa HI restriction site. Thus Bsa HI digestion will give a different restriction pattern as between normal and mutant alleles, since in this case the normal sequence will be cleaved at this site by Bsa HI, whereas the mutant sequence will not. Therefore, a further aspect of the present invention provides a method of diagnosing or screening for bovine α-mannosidosis comprising detecting the presence or absence of α-mannosidosis-causing mutations in the gene encoding bovine LAMAN using a restriction enzyme.

In view of the fact that restriction sites may conveniently be created or removed in the α-mannosidosis causing mutant alleles of the gene encoding bovine LAMAN, detection by RFLP represents a particularly preferred method and comprises a further aspect of the present invention. PCR-based RFLP analysis was developed to provide a non-radioactive method for fast and simple detection of mutations. This method relies upon the introduction of restriction endonuclease sites permitting differential cleavage between normal and mutant sequences. The α-mannosidosis causing mutation results in a change in the restriction sites in the gene and so there is a change in the pattern when the digested fragments resulting from treatment with a particular restriction enzyme are separated on a gel. The appearance and/or disappearance of a particular sized fragment, indicated by a band on a gel, is a simple way of detecting a mutant allele.

Clearly, any analysis of DNA potentially containing the disease causing mutation would be enhanced by the use in the test of an amplified amount of the particular DNA fragment around the mutation site. If the fragment of interest can be amplified, small amounts of starting material may be employed, for example, a few hair roots. As mentioned above, any of the in vitro amplification techniques known and described in the literature may be used. The polymerase chain reaction (PCR) and its modifications will generally be the principal method of choice. PCR techniques require primer sequences which are complementary to DNA sequences upstream and downstream of the disease causing mutation. These primers are used to amplify the DNA region that is located between them. The identification of suitable oligonucleotide primers constitutes a further aspect of the present invention. Suitable primers may be designed with reference to the cDNA and genomic sequences of the bovine LAMAN gene which are provided according to the present invention. Thus, for example, primers may be based on flanking sequences in either the cDNA or genomic DNA, which flank the site of the mutation, and suitable sequences may be selected from FIGS. 1 and 2 (SEQ ID Nos. 1 and 2) provided herein. In the case of the genomic bovine LAMAN sequence, primers may be based on both flanking intron and exon sequences. For detection of the mutation in Angus and Angus-related breeds eg. Murray Grey cattle the following primer sequences are preferred:

5'CGCTGGACAC CCTAGCCTTA GGA 3' (SEQ ID No.5) or

5'CGCAGGACACCCTAGCCTTAG-3' (SEQ ID No.7) and 5'CCTTGCTATT GTTTTAAGCC TCTAAGTTT GTGGT 3' (SEQ ID No.6)

The resulting amplified fragment is 296 base pairs and includes the nucleotide $T_{961}$ that is mutated in α-mannosidosis. In all cases, numbering of the nucleotides starts at the translation initiation codon. FIG. 4 shows the DNA sequence (SEQ ID No. 4) that is amplified during the PCR, indicates the primers (SEQ ID Nos. 5 and 6) and the mutated nucleotide. This T to C mutation introduces a further cleavage site for the restriction endonuclease Mnl I.

In order to detect the mutation in Galloway cattle, the following primers are preferred:
5'GGGCTGCGCG TGTCCTCCAC AA 3' (SEQ ID No. 8)and
5'CAGAAAATCG TGAGGGAACT GGTG 3' (SEQ ID No. 9).

The following primer pair is also used to detect the mutation in Galloway cattle:
5'CGCAGGACACCCTAGCCTTAGGA 3' (SEQ ID No.10)
5'CCTTGCTATTGTTTTAAGCCTCTAAGTTTGTGGT 3' (SEQ ID No. 6).

This results in the amplification of a 1,700 base pair fragment or a 360 base pair fragment which includes the disease causing mutation $G_{662}$ to A. This mutation removes a restriction site for the restriction endonuclease Bsa HI which results in different size fragments on digestion, easily detected on separation by gel electrophoresis.

Oligonucleotide primers may also be used in PCR or other in vitro amplification or primer extension-based methods of detecting mutations, eg. by PCR-SSP (PCR amplification with sequence specific primers, a technique for detecting print mutations or allelic variations, traditionally used in tissue typing, see eg. Bunce et al., 1995, Tissue Antigens, 45, 81–90) or the ARMS Technique of Zeneca for detecting variant nucleotide sequences as described in EP-A-0332435.

Thus for example, primers may be designed wherein the terminal base of the primer at the 3' end is designed to be complementary either to the normal or mutant base, such that there is a terminal mismatch in the primer, either with the mutant or with the normal allele; amplification is much more efficient where there is a terminal match as opposed to mismatch, allowing the presence or absence of the mutation to be discriminated, according to the amount of amplified product obtained.

The invention also extends to kits for the detection of disease causing mutations which comprise at least one oligonucleotide primer sequence according to the invention. Such kits normally also contain additional components such as another oligonucleotide primer which hybridises to the opposite strand of the target DNA and/or a restriction endonuclease sensitive to a bovine α-mannosidosis causing mutation The following examples are given by way of illustration only with reference to the following figures.

BRIEF DESCRIPTION OF THE FIGURES

FIG. 1 shows the nucleotide sequence of bovine LAMAN cDNA (SEQ ID NO.1) and the deduced amino acid sequence (SEQ ID NO.2). The amino acid sequence is shown in single letter code below the nucleotide sequence. Both nucleotides and amino acids are numbered from the start of the open reading frame. The amino acid sequences colinear with N-terminal peptide data are double underlined. Amino acid sequences that exhibit similarities with N-terminal amino acid sequences of human LAMAN peptides d and e are single underlined. The predicted polyadenylation signal (ATTAAA) is marked in bold.

FIG. 2 shows the partial nucleotide sequence of bovine LAMAN genomic DNA (SEQ ID No. 3). The exons are written in upper case and the introns in lower case. Gaps in the intron sequence are indicated by askerisks (*)

FIG. 3 presents a scheme showing the different fragments produced when amplified DNA encoding part of the LAMAN gene in Angus cattle is treated with the restriction enzyme Mnl I.

FIG. 4 shows a DNA sequence encompassing the $T_{961}$ mutation that is amplified by PCR (SEQ ID No. 4). The oligonucleotide primers are shown in small letters and the thymine nucleotide which is replaced by cystine in the mutated allele is surrounded by a box.

FIG. 7B. right side) and molecular masses of the LAMAN peptides (A, right side) are shown. In FIG. 7C, various types of oligosaccharide chains are: (■) endo H-resistant; (□) endo H-sensitive; (◨) mixture of endo H-resistant and sensitive. Partial N-glycosylation is symbolized by brackets and arcs symbolize disulphide bridges.

FIG. 10 shows the sequences of the intron/exon boundaries of the bovine LAMAN gene (SEQ ID Nos. 59–104). The exon sequences are shown in upper case letters, the intron sequences in lower case.

Figure 5:
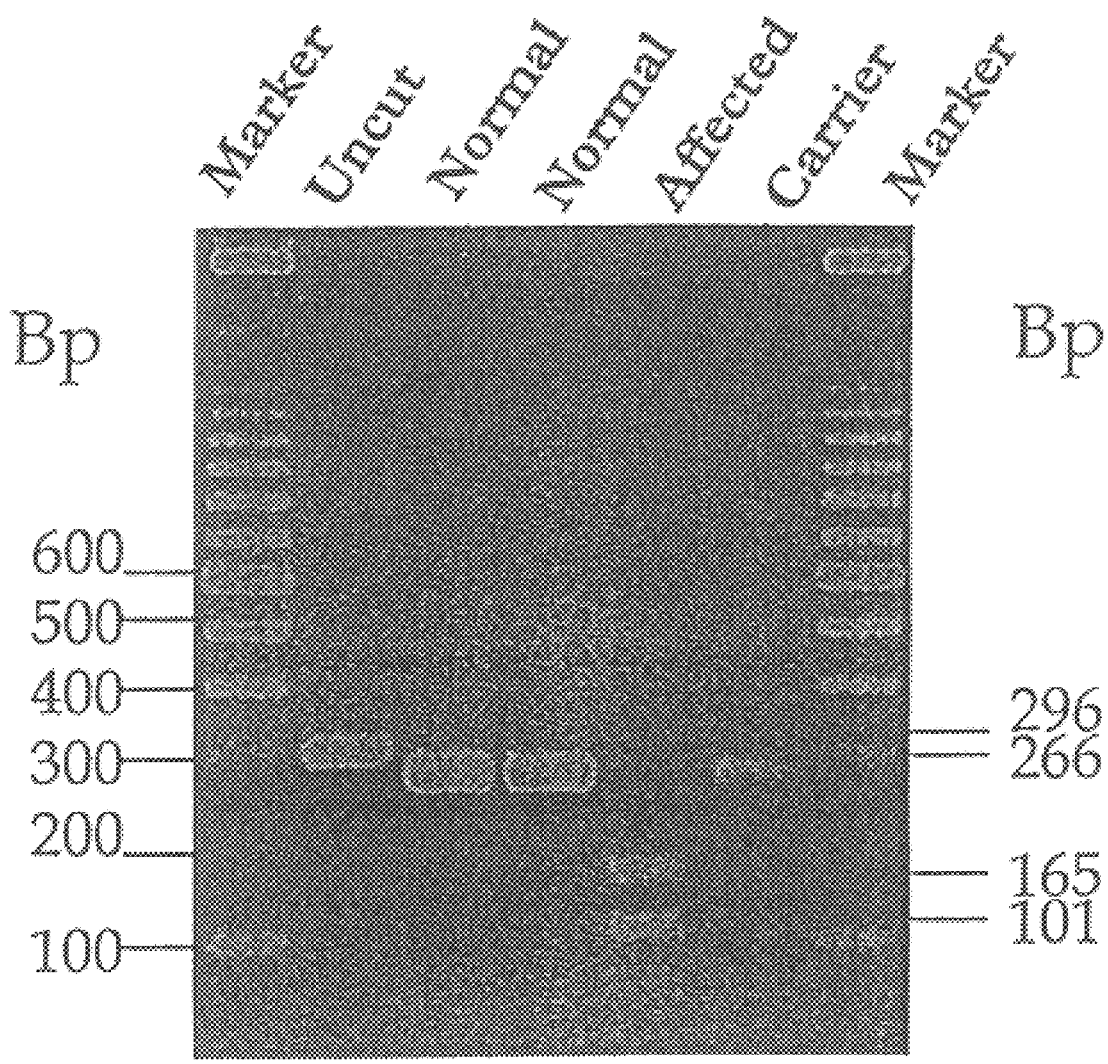
FIG. 5 is an Agarose gel stained with ethidium bromide showing the results of electrophoresis following digestion of LAMAN DNA with Mnl I.

Part B, in the left gel: shows Bsa HI digestion of a 1700 bp PCR product amplified from Galloway animals using the primer combination mp30/mp262. Amplicons from normal animals are digested to four fragments (123 bp+380 bp+420 bp+780 bp), while for affected three fragments are observed (123 bp+380 bp+1200 bp). In carriers all fragments are present.

In the right gel: Mnl I digestion of 295 bp amplicaons from Angus animals using primers mpi6F and mpi7R are shown. Digestion of amplicons from normal results in fragments of 29 bp+266 bp, while amplicons from affected are digested to fragments of 29 bp+101 bp+165 bp. In carriers all fragments are observed.

EXAMPLE 1

Polymerase chain reaction (PCR) amplification of the sequence that encompass the $T_{961} \to C$ ($Phe_{271} \to Leu$) mutation The method includes the amplification of a DNA fragment by PCR. The amplified fragment is 296bp including the nucleotide $Tg_{61}$ that is mutated in α-mannosidosis. FIG. 4 shows the DNA sequence that is amplified by PCR. Oligonucleotide primers for amplification are called 1 and 2. Sequences for the primers are respectively 5'CGCTGGACAC CCTAGCCTTA GGA 3' (SEQ ID No.5) (1) and
5'CCTTGCTATT GTTTTAAGCC TCTAAGTTT GTGGT 3' (SEQ ID No.6) (2).

The PCR amplification is typically carried out in a 100 μl volume with 20 pmole of each primer, 100 ng genomic DNA, 250 μl of each DNTP, 2 U Taq DNA polymerase, 2 mM $Mg^{2+}$ and 1×PCR buffer (10 mM HCl, pH 8.3 containing 50 mM KCl). PCR conditions are: 95° C. for 5 minutes followed by 34 cycles where the temperature varies between 66° C. for 2 minutes and 94° C. for 1 minute. Finally the reaction mixture is incubated for 7 minutes at 72° C.

Analysis of the PCR product

The PCR product is cut by the restriction enzyme Mnl I (P. Brinkley, et al., 1991, Gene, vol. 100, 2670–2682) at 37° C. for three hours. A Mnl I restriction site was introduced in primer 2 (underlined in FIG. 4). This site fuctions as a positive control for the Mnl I enzyme activity. The PCR product from normal cattle will be cut into fragments of 29 bp+267 bp whereas affected cattle with the $T_{961} \rightarrow C$ ($Phe_{271} \rightarrow Leu$) mutation will but cut into DNA fragments of 29 bp+101 bp+166 bp. The carriers have both a normal and a mutated allele. Thus all the four DNA fragments will be present after Mnl I cutting of the PCR products from carriers. The fragments are separated by agarose gel electrophoresis. A 4% agarose gel with 1×TBE (89 mM Tris-borate, pH 8.0 containing 2 mM EDTA) as electrophoresis buffer is used. The DNA fragments are visualized using ethidium bromide staining and ultraviolet illumination (J. Sambrook, et al., 1989, In: Molecular Cloning: A Laboratory Manual). An example of an agarose gel electrophoresis is shown in FIG. 5.

EXAMPLE 2

Purification, cDNA sequencing and genomic organisation of bovine lysosomal α-mannosidase; characterisation of two mutations that cause bovine α-mannosidosis Enzyme assay Lysomal α-mannosidase was assayed in 0.1 M acetate buffer, pH 4.5 and 4 mM p-nitrophenyl α-D-mannopyranoside (SIGMA) at 37° C. Biochem. J., 71: 318–323) or in 0.1 M acetate buffer, pH 3.7 and 4 mM 4-methylumbelliferyl α-D-mannopyranoside (SIGMA). One unit of activity is defined as the amount of enzyme that liberates one μmol of p-nitrophenol per min under the assay conditions.

Purification of α-mannosidase (summarized in Table 1 below)

TABLE 1

Purification of bovine kidney LAMAN

| Purification step | Total Protein (mg) | Total activity (units) | Specific activity (units/mg) | Purification (fold) | Yield (%) |
|---|---|---|---|---|---|
| Crude extract (10 kg of kidney) | 80000 | 1000 | 0.013 | 1 | 100 |
| Heat treatment (60° C., 30 min) | 30000 | 900 | 0.03 | 2.3 | 90 |
| Concanavalin A-sepharose | 1100 | 720 | 0.65 | 50 | 72 |
| Hydroxylapatite | 230 | 600 | 2.6 | 200 | 60 |
| DEAE anion exchange | 10 | 150 | 15 | 1154 | 15 |
| Superdex 200 gel filtration | 5 | 100 | 20 | 1538 | 10 |

The first step was carried out at 4° C., while all the following steps were performed at room temperature.

Step 1 Preparation of a crude extract

Ten kg of bovine (Norwegian red cattle) kidney that was obtained freshly from a local slaughterhouse was cut into small pieces and homogenized in 0.075 M acetic acid/0.15 M NaCl 1:2 (w:v) using a Waring blendor. The homogenate was centrifuged at 10.000 g for 10 min. To the supernatant was added ammoniumsulfate to 35% saturation and stirred for at least 4 h and centrifuged at 10.000 g for 10 min. Ammoniumsulfate was then added to 75% saturation and after stirring the solution was centrifuged as before. The resulting pellet was dissolved in a minimum amount of 0.05 M sodium phosphate buffer, pH 7.4/0.15 M NaCl (PBS). The final volume was typically 41 and the solution was labelled "crude extract".

Step 2 Heat treatment

Since bovine lysosomal α-mannosidase is stable at high temp. (Winchester et al., 1976, Biochem. J., 157: 183–188) the crude extract was brought to 60° C. and kept at that temperature for 20 min. The precipitate was removed by centrifugation at 10,000 g for 10 min.

Step 3 Concanavaline A-Sepharose

To the supernatant was added 50 ml concanavalin A (con A)-Sepharose (Pharmacia). The suspension was mixed for 2 h using a magnetic stirrer, and then run through a column. The resulting column of con A-Sepharose (2.5×10 cm) was washed with PBS. LAMAN was eluted by 200 ml PBS containing 0.2 M α-methylmannoside.

Step 4 Hydroxylavatite chromatography

The eluate from the con A-Sepharose was applied to a 1.5×15 cm column of hydroxylapatite (Biogel HTP, Bio-Rad) equilibrated with PBS. Elution was carried out with 0.25 M sodium-phosphate, pH 7.4/0.15 M NaCl. The eluate was dialysed against 4 1 or 0.02 M Tris/HCl, pH 7.6 with two shifts.

Step 5 O-Sepharose anion exchange chromatography

The dialysate was applied to a Q-Sepharose (Pharmacia) column (2×11 cm) equilibrated with 0.02 M Tris/HCl, pH 7.6 at a flow rate of 0.8 ml/min. LAMAN activity appeared in the run through and was concentrated through an Amicon ultrafiltration unit fitted with a YM 30 membrane.

Step 6 Superdex 200 size exclusion chromatography

The concentrated sample was applied to Superdex 200 (Pharmacia) (1.5×60 cm) equilibrated with PBS at a flow rate of 0.4 ml/min. The fractions containing LAMAN activity were collected and concentrated through Centricon 30 microconcentrator (Amicon).

Aminoterminal sequencing

N-terminal amino acid sequencing of the LAMAN peptides were carried out as previously described (Tollersrud and Aronson (1989) Biochemical Journal, 260 pp 101–108).

Generation of antibodies

Polyclonal antisera were obtained by immunization of male Chinchilla rabbits with native LAMAN, the 67 kDa (peptide abc) and the 38 kDa (peptide d) peptide respectively according to standard protocols. Affinity purified antibodies against the 35 kDa peptide (peptide a) and the 22 kDa peptide (peptide c) were prepared by incubating poly (vinylidine difluoride) (PVDF)-membrane strips (Immobilon™, Millipore), onto which the 35 kDa peptide or the 22 kDa peptide had been blotted, with ⅕ diluted anti(67 kDa peptide )serum in 0.01 M Tris/HCl, pH 8.0/0.15 M NaCl/0.05% Tween 20 (TBST). The samples were kept 1 hour at room temp. and overnight at 4° C. The pieces of membrane were washed three times with PBS and eluted with 0.2 M glycine, pH 2.8. The eluates were immediately neutralized by ⅓ volume of 10×PBS.

Isolation and sequencing of laman cDNA

Figure 6:
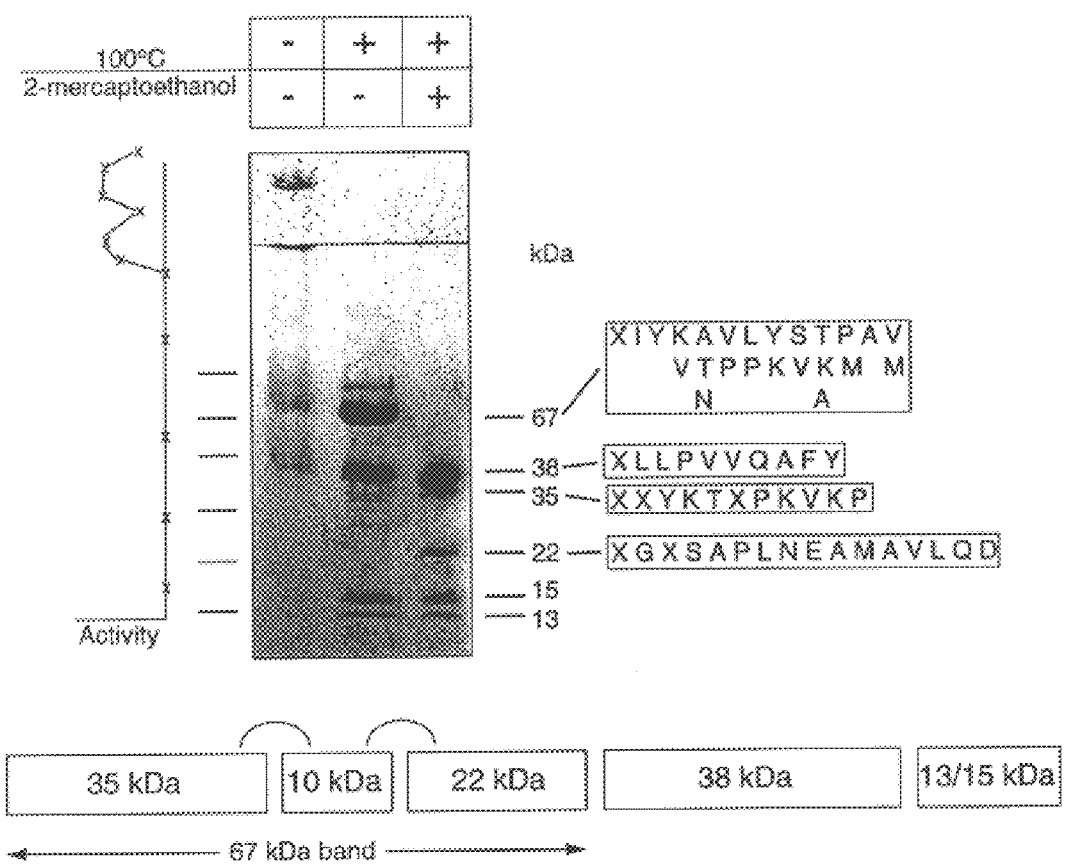
FIG. 6 illustrates SDS/PAGE and N-terminal amino acid sequencing. About 1 mg/ml of purified LAMAN was subjected to SDS/PAGE either without pretreatment (left lane), prior heat denaturation (middle lane) or both heat and reduction (right lane). The gel was stained with coomassie blue. For activity measurements the enzyme was applied to SDS/PAGE without pretreatment. After the run the gel was cut into several pieces, transferred into tubes containing PBS and following overnight diffusion the enzyme activity was determined in the solution. For N-terminal sequencing the peptides were transferred to a PVDF-membrane by electroblotting and sequenced by Edman degradation as described. The peptide sequences shown are SEQ ID Nos. 55–58. The 67 kDa band exhibited more than one amino acid in several of the cycles of Edman degradation (upper sequence, right side SEQ ID No. 55) indicating the presence of more than one N-terminal sequence within this band. Molecular mass markers as described are indicated on the left side. The molecular masses of the LAMAN peptides are shown on the right side. A model of bovine LAMAN with arcs symbolizing disulphide bridges between peptides is also shown.

Degenerate oligonucleotide primers were designed to amplify LAMAN cDNA from a bovine kidney Lambda ZAP cDNA library (Stratagen). The forward primer aaMA1F: 5' ATITACAAIACIGTICCIAAIGTIAAICC 3' (SEQ ID No. 11) was deduced from amino acids 2–11 in the 35 kDa peptide (FIG. 6) with the ambiguous amino acids in pos. 2 and 6 assigned Ile and Val respectively. The reverse primer abMA1R: 5' ACIGCCATIGCITCATTIAGIGGIGC 3' (SEQ ID No. 12) was deduced from amino acids 5–13 of the 22 kDa peptide (FIG. 6). To obtain bovine laman cDNA, DNA extracted from the library was subjected to a two stage PCR. In the first round of 10 cycles the primer concentrations were 10 fM and they were increased to 0.1 nM for a further 30 cycles. For each cycle denaturation for 4 min at 94° C. followed by annealing at 43° C. for 3 min and extension at 70° C. for 3 minutes. The resulting PCR product of about 1200 bp was cloned into the TA-cloning vector pCRII, as described by the manufactorer (Invitrogen) and then subcloned in both orientations into M13 mp18 by EcoRI digestion, gel purification and ligation. The clone was sequenced with the M13-40 universal primer and by primer walking. The cloned PCR fragment was used to screen $10^6$ plaques from the bovine kidney Lambda ZAP cDNA library. Three independent clones were isolated, subcloned into M13, and sequenced in both orientations. The 5' end of the cDNA contained an inverted repeat likely to form a stem-loop structure with a stem size of 58 nts and a loop size of 148 nts. This inverted repeat was probably created by abberant cDNA synthesis during the library construction.

Isolation of a 5' cDNA fragment

Genomic DNA isolated from bovine fibroblasts from an Angus bull (cc 87/888) was digested with ApaI, diluted to 2 μg/ml and religated. The circularised DNA was subjected to PCR using the reverse primer mph266R 5'AGAGAG-GCGGGAGCGGTGG3' (position 106–88) and the forward primer mp30 5'CAGAAAATCGTGAGGGAACTGGTG3' (position 409–432) SEQ ID No. 14. After an initial denaturation at 94° C. for 5 min, 7 cycles at 98° C. for 20 sec and extension at 70° C. for 2 min were followed by 34 cycles at 98° C. and extension a 67° C. The 1500 bp amplicon product produced from the circularized religated ApaI digest was cloned into pCRII and partially sequenced. A part of this sequence was used as forward primer mp5UT1F 5'GTG-GCGGCGGCGGCTGCAGA3' (position 4–23 SEQ ID No. 15) in combination with reverse primer mp262 5'GGGC-TACGCGTGTCCTCCACAA3' (position 836–857) SEQ ID No. 16 obtain an RT/PCR product of 800 bp that constituted a 5' part of the LAMAN cDNA.

Genomic organization

PCR with Taq DNA polymerase and with a mixture of Taq and Pwo DNA polymerases (Expand Long Template PCR System—Boehringer Mannheim) was used to amplify fragments from genomic DNA isolated from a Charolais bull. For each fragment annealing conditions were optimised to obtain a single band evident upon electrophoresis in agarose. Length of each amplified fragment were determined by comparison with molecular weight markers (Boehrienger Mannheim and Gibco BRL). Fragments amplified from genomic DNA were purified by PEG precipitation and sequenced with the primers in the following Table.

Primers used for the determination of the genomic organisation (SEQ ID Nos. 17–53)

| Primer#[a] | Location | Position | Sequence of primer 5'—3' |
|---|---|---|---|
| EMAI 99 | e-1 | 88–106 | CCACCGCTCCCGCCTCTCT |
| EMAI 146 | i-1 | -38/-19 | ACTGACAGAGTGAGTGTGTG |
| EMAI 88R | e-2 | 224–206 | TCATCATGTGTGTGAGGCA |
| EMAI 185 | e-3 | 317–338 | TCTCTTCCTTGCTGGCGAATCC |
| EMAI 81 | e-3 | 409–432 | CAGAAAATCGTGAGGGAACTGGTG |
| EMAI 148 | i-3/e-4 | -7/440–451 | GGAACAGGACGCCTAGAGT |
| EMAI 83R | e-4 | 534–513 | CGCAGTCTGAGTGTCATCTGG |
| EMAI 84 | e-5 | 694–714 | AAGACGCTGCAGATGGAGCAGG |
| EMAI 149R | e-5/i-5 | 765–766/+18 | TCCACTCTACCACCTTACTG |
| EMAI 82R | e-6 | 857–836 | GGGCTACGCGTGTCCTCCACAA |
| EMAI 142 | e-6 | 836–855 | TTGTGGAGGACACGCGTAGCCC |
| EMAI 100R | e-7 | 990–971 | GAACCACGTGTTGGCATTCT |
| EMAI 109R | i-7 | +135/+107 | CCTTGCTATTGTTTTAAGCCTCTAAGTTTG |
| EMAI 85 | e-7 | 1002–1024 | CAAGCTCATCCAGTTGGTCAATG |
| EMAI 141 | e-8 | 1046–1067 | TCCGCGTCAATGTTCTCTACTC |
| EMAI 80R | e-9 | 1124–1102 | TTCACTGACCAGCTGAGGTTGGC |
| EMAI 139R | e-11 | 1364–1344 | GAGGTACCACTGACTGCATCA |
| EMAI 143 | e-11 | 1342–1363 | CATGATGCAGTCAGTGGTACCT |

-continued

| Primer#[a] | Location | Position | Sequence of primer 5'—3' |
|---|---|---|---|
| EMAI 140 | e-12 | 1482–1502 | TTGTCGCAAGCTCAACATCAG |
| EMAI 139R | e-12 | 1531–1511 | TCTCTGCTGTCTGCGTGAGTG |
| EMAI 89 | e-14 | 1677–1699 | TCAGGAGCTGCTTTTCTCAGCCT |
| EMAI 144R | e-14 | 1737–1718 | GGAGACTGAGTAGATGCTGA |
| EMAI 97R | e-15 | 1892–1869 | TAGAAGGCTTGGCGAACAGGCAGC |
| EMAI 91 | e-16 | 1941–1959 | GGTGCCTACATCTTCAGAC |
| EMAI 134R | i-16 | +79/+61 | CCTCACAAGGCACATCACG |
| EMAI 135 | i-16 | −46/−28 | GCTCAGGTGCACGCTTACA |
| EMAI 92 | e-18 | 2216–2194 | CGGCCATTGCTGTCAGTGAGAA |
| EMAI 94 | e-19 | 2286–2305 | AAATTACTATCCAGTCAACA |
| EMAI 133R | i-19 | +79/+60 | GGAGATGTCAAGAACAGGTG |
| EMAI 90R | e-21 | 2502–2480 | CAGCACGAGGTGACGTCCTCGCA |
| EMAI 95 | e-21 | 2553–2574 | GGAGGTCCTGGCCCCGCAGGT |
| EMAI 128 | e-22/i-22 | 2784–2787/+17 | GACGGTGAGGATAGAGATGGA |
| EMAI 96R | e-23 | 2851–2830 | GGAGCTGGTTGGCCGCCAGCGT |
| EMAI 93 | e-23 | 2859–2879 | CGCCTCCAGGCTCCAGTGGAC |
| EMAI 127R | i-23 | +133/+110 | TCTGAACACCGACTTACTCCGACC |
| EMAI 126R | i-23 | −70/−87 | CCTGAACACAGACATACC |
| EMAI 86R | e-24 | 3097–3072 | GGCTTTCATTGGTGGTAGTAAGAGCA |

[a]R at the end refers to reverse primer

Western blotting

Purified LAMAN (0.1 mg/ml) was subjected to SDS/PAGE on a Phast gel system (Pharmacia) using a gradient of 8–25% polyacrylamide. After electrophoresis, the gel was overlayed with a PVDF membrane, and blotting was carried out by diffusion at 70° C. for 2 hours. The membrane was blocked for 20 minutes with 2% (w/v) bovine serum albumin and incubated with 1/500 diluted antiserum in TBST for 30 minutes at room temperature. The immuno-complex was detected with a secondary antibody/alkaline phosphatase conjugate kit (Bio-Rad).

SDS/PAGE

SDS/PAGE was carried out with the Phast system from Pharmacia using an 8–25% gradient of polyacrylamide or the mini gel apparatus from Bio-Rad with 10% polyacrylamide in separating gel. For molecular mass analysis the standards were (Pharmacia): α-lactalbumin (14.4 kDa), soyabean trypsin inhibitor (20.1 kDa), carbonic anhydrase (30 kDa), ovalbumin (43 kDa), bovine serum albumin (67 kDa) and phosphorylase b (94 kDa).

Deglycosylation

10 μl LAMAN (1 mg/ml) was added SDS to a final concentration of 1% and kept in boiling water for 2 minutes. 90 μl 20 mM sodiumphosphate buffer, pH 7.2/50 mM-EDTA/0.5% Nonidet P-40 was added. After cooling 0.4 units peptide:N-glycanase F (PNGase F) or 2 units endoglycosidase H (endo H) (Boehringer Mannheim) was added and the solution incubated at 37° C. overnight. The deglycosylated enzyme was analyzed by SDS/PAGE.

Purification of LAMAN

The purification procedure is summarized in Table 1. The final preparation had a specific activity of 20 U/mg, which is in the same order as previous reports on purified LAMANS.

The purity was further assessed by SDS/PAGE. The enzyme remained active after SDS/PAGE and was detected at the point of application and the stacking/separating gel interface (FIG. 6). These bands probably contained the native LAMAN complex that migrated slowly due to the lack of sufficient SDS-coating, as previously reported for two other SDS-resistant enzymes, superoxide dismutase and glycosylasparaginase (Tollersrud and Aronson, 1989). Four faint lower molecular weight bands were also detected (FIG. 6, left lane) that presumably were SDS-coated peptides resulting from partial denaturation of the native complex. The increased staining intensity of these bands after heat-denaturation concomitant with the loss of the two activity containing bands confirmed that they were dissociated peptides of the native LAMAN complex. The absence of bands that did not exhibit this correlation indicated that the enzyme was pure. Its isoelectric point was about 9.

Bovine LAMAN consists of 5 glycopeptides

Gel filtration on Superdex 200 indicate that the molecular mass of native LAMAN is approximately 250 kDa. FIG. 6 illustrates that there are four peptides within LAMAN (center lane) and that breaking disulphide bonds fractionates the 67 kDa peptides to 35 kDa and 22 kDa fragments (right lane) leaving a putative 10 kDa fragment undetected. With knowledge of the multiple N-terminal amino acid sequences of the 67 kDa peptide and of the 35 kDa and 22 kDa fragments (FIG. 6, right side) the deduced N-terminal sequence of the putative 10 kDa peptide would be NH$_2$XXXVNXXYST SEQ ID No. 54.

Figure 7:
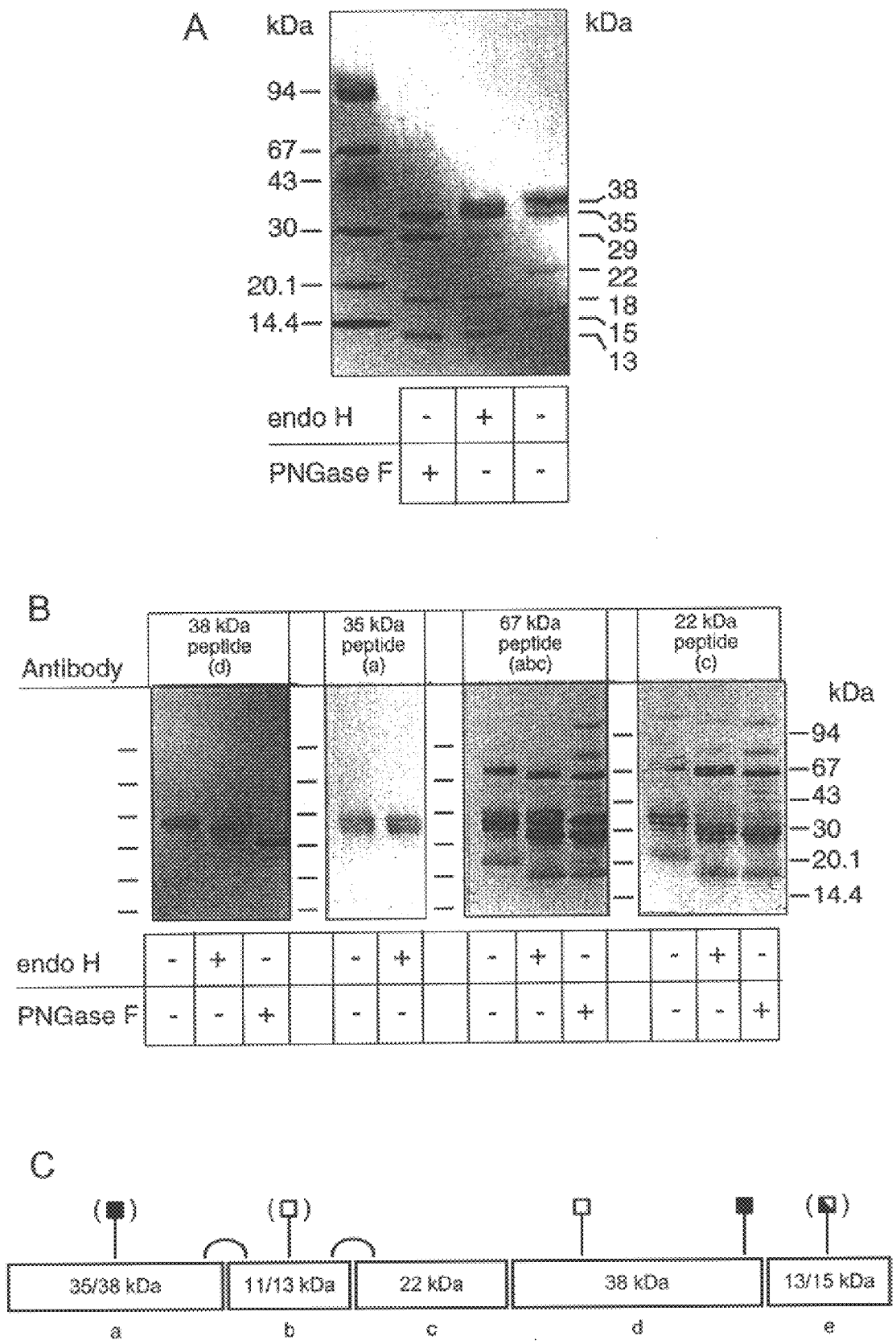
FIGS. 7A, 7B and 7C show molecular shift analysis after endoglycosidase H- and PNGase F-treatments. About 1 mg/ml of LAMAN was heat denatured and treated with endo H and PNGase F. The glycosidase-treated samples were subjected to SDS/PAGE after reduction by β-mercaptoethanol and stained with coomassie blue (FIG. 7A) or blotted onto a PVDF-membrane and immunostained using peptide-specific antisera (FIG. 7B). Molecular mass standards (FIG. 7A, left side.
Figure 8:
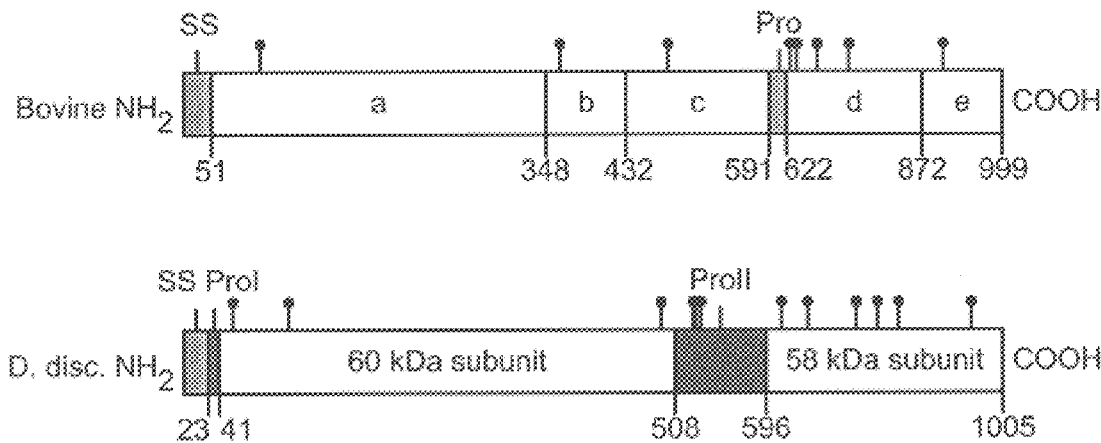
FIG. 8 shows the organisation of the LAMAN precursor. The six predicted cleavage sites of the LAMAN precursor are illustrated and the resulting products are designated as the signal peptide (SS), peptide a, peptide b, peptide c, pro, peptide d and peptide e. The amino acid position at each cleavage is listed below the diagram. Potential N-glycosylation sites are indicated by black circles. The organisation of D. disc. LAMAN precursor is illustrated below the bovine LAMAN figure as a comparison.

Panels A and B of FIG. 7 illustrates the effects of endo H and PNGase F treatments upon the various peptides. Peptides in panel A were detected with coomassie blue and those in panel B immunostained with peptide specific antibodies. The peptides were designated a–e according to their position in the one chain precursor as illustrated in FIG. 8.

Antibodies against the 35 kDa peptide (peptide a) recognized a 38 kDa endo H-resistant form (FIG. 7B). However, following PNGase F treatment only a 35 kDa peptide was detected (FIG. 7B, left lane) indicating that this 38 kDa peptide is a glycosylated variant of the 35 kDa peptide and that the sugar chain is of complex type.

Antibodies against the 22 kDa peptide (peptide c) recognized 3 additional peptides of 70 kDa, 35 kDa and 33 kDa (FIG. 7B, right blot) that were present in low concentrations as they were not detected in coomassie blue stained gel. Given molecular masses it is probable that the 70 kDa peptide is a one chain precursor of the 67 kDa band consisting of peptides a, b and c. Similarly, the 35 kDa and 33 kDa bands are most likely precursors of the 22 kDa peptic and the putative 10 kDa peptide (peptide b). After both endo H and PNGase F treatments the 35 kDa and 33 kDa peptides detected with the anti (22 kDa peptide)body, merged to a 29 kDa band (FIG. 7B, right blot) indicating that their sugar chains are not of the complex type. As both PNGase F and endo H treatments transformed the 22 kDa to an 18 kDa peptide (FIGS. 7A and 7B) the 29 kDa unglycosylated band was composed of an 11 Da peptide in addition to the 18 kDa peptide. This 11 kDa peptide is probably the putative 10 kDa peptide that was not observed on SDS/PAGE (FIG. 6). It is probable then that the 33 kDa and 35 kDa peptides that crossreacted with anti (22 kDa peptide) body contain an unglycosylated and a glycosylated form of this 11 kDa peptide respectively.

The 38 kDa peptide (peptide d) was catabolised to a 35 kDa band after endo H-treatment and to 29 kDa after PNGase F-treatment (FIG. 7, panel B, left blot) suggesting that the peptide had one sugar chain of high mannose and two of the complex type. After PNGase F-treatment the 15 kDa peptide (peptide e) merged with the 13 kDa peptide suggesting that the former is a N-glycosylated variant of the latter. However, some 15 kDa peptide persisted after endo H-treatment. Partial N-glycosylation of lysosomal enzymes has been reported previously. A model of the peptides and their N-glycosylation pattern is shown (FIG. 7C).

The LAMAN peptides originate from a single gene

Figure 1:
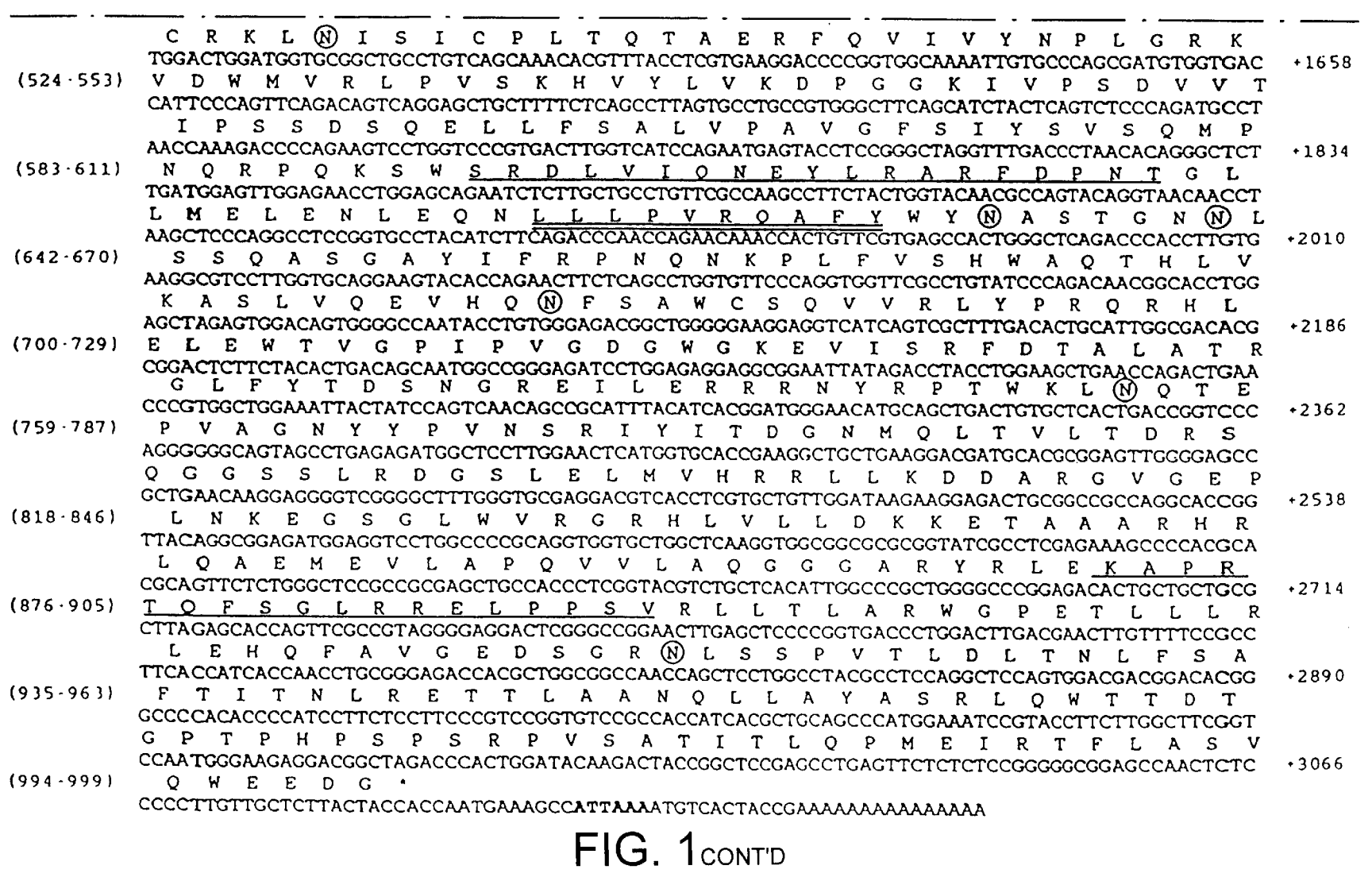

The aminoterminal amino acid sequences of the 35/38 kDa (peptide a) and 22 kDa (peptide c) peptides exhibited 40% identity with two internal sequences within D. disc. LAMAN (Schatzle et al., 1992) separated by 376 amino acids. With degenerate oligonucleotides deduced from these amino acid sequences as primers a 1200 bp fragment was amplified from a bovine kidney lambda ZAP cDNA library. The amino acid sequence deduced from the amplified fragment was 49% identical with D. disc. LAMAN and contained an amino acid sequence similar to the aminoterminus of peptide b. The 1200 bp amplified product was used as a probe to screen the bovine kidney λ ZAP library. Sequencing the 3300 bp insert in a positive clone revealed an open reading frame. The deduced amino acid sequence contained the aminotermini of each of the LAMAN peptides and a 136 bp untranslated region with a poly A signal 13 bp upstream of a poly A tail (FIG. 1). The 5' end of the cDNA had an inverted loop of 200 bp that was considered likely to be an artifact of the library construction. Primers based on the sequence of a circularised genomic fragment from an upstream region of the laman gene were used in RT/PCR to obtain the 5' end of the cDNA. Two in frame ATGs were detected that were 150 and 288 nucleotides respectively upstream of the first nucleotide encoding the N-terminus of peptide a. Two forward primers were constructed that corresponded to sequences immediately upstream of each ATG codon and were used in combination with a reverse primer mp262 for RT/PCR as detailed in the experimental section. Only the primer immediately upstream of the second ATG resulted in a PCR product of the expected size of 800 bp, while both combinations resulted in the expected size of about 2000 bp when PCR was carried out using genomic DNA as template (not shown). Thus the second ATG is probably the translation initiation site. This region conformed with the Kozak concensus sequence (Kozak, 1991). The DNA sequences from the RT/PCR product and the λ ZAP cDNA clone were combined to yield a full length cDNA sequence encoding the entire bovine LAMAN polypeptide (FIG. 1).

A comparison of the molecular masses of the deglycosylated peptides determined by SDS/PAGE and by calculation from the deduced amino acid sequence revealed that they were similar (Table 2) except for peptide c that was 21.3 kDa according to the deduced cDNA sequence, while the Mr of the deglycosylated peptide was 18 kDa according to SDS/PAGE.

TABLE 2

Comparison between molecular masses as judged by SDS/PAGE and calculated from the deduced cDNA sequence

| Peptide | $M_r$ (kDa) on SDS/PAGE | $M_r$ (kDa) on SDS/PAGE after PNGase F | $M_r$ (kDa) calc. from deduced cDNA seq. | $M_r$-shift (kDa) after PNGase F | Glycosylation site from deduced cDNA |
|---|---|---|---|---|---|
| a | 35/38 | 35 | 34.5 | 0/3 | 1 |
| b | 11/13 | 11 | 9.6 | 0/2 | 1 |
| c | 22 | 18 | 17.4 | 4 | 1 |
| d | 38 | 29 | 28.4 | 9 | 4 |
| e | 13/15 | 13 | 14.1 | 0/2 | 1 |
| total | 119/126 | 106 | 104 | 13/20 | 8 |

In human LAMAN there is a cleavage site corresponding to bovine LAMAN position 591 that is 31 amino acids N-terminally to the cleavage site that generated the N-terminus of peptide d. Assuming that this human cleavage site is conserved in bovine LAMAN the Mr of peptide c from the deduced cDNA sequence would be in agreement with its relative migration on SDS/PAGE after deglycosylation (Table 2). A model of the cleavage pattern and N-glycosylation sites is illustrated (FIG. 8). In this model the peptides are named a to e according to their original position relative to the N-terminus of the LAMAN one chain precursor.

Alpha-mannosidosis among Angus cattle

The α-mannosidase activity in a liver extract from affected Angus cattle was 0.3% of normal as previously reported by Healy et al., 1990, Res. Vet. Sci., 49: 82–84. Half of this activity was immunoprecipitated indicating that LAMAN was expressed at 0.15% of normal activity. The residual activity that did not immunoprecipitate was also found in a normal liver extract. An acid α-mannosidase activity from human Alpha-mannosidosis fibroblasts with similar properties has previously been reported indicating that this is a different gene product. Western blot analysis of fibroblast extracts showed a decrease of expression of peptide abc.

Figure 9:
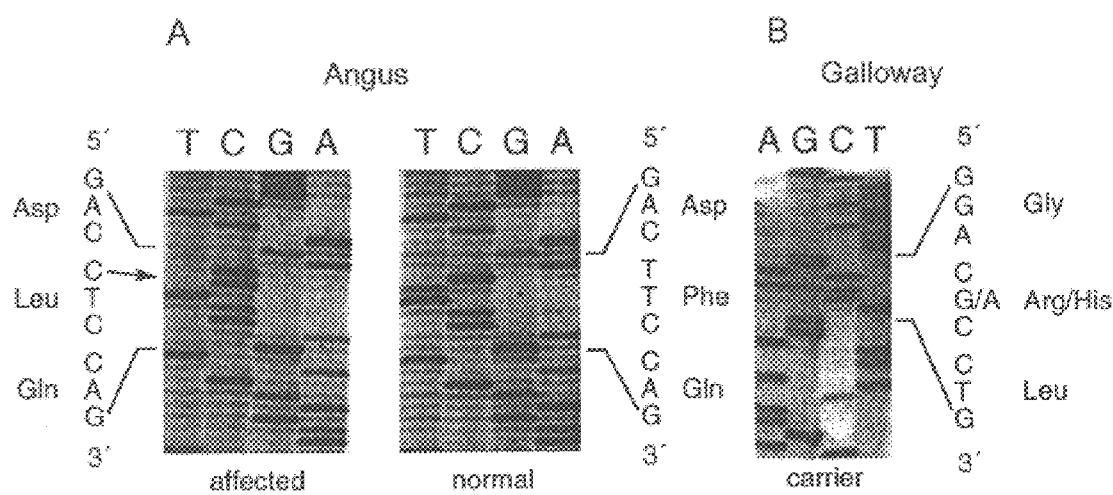
FIGS. 9A and 9B show mutation detection in α-mannosidosis affected Angus and Galloway cattle. Partial sequence of the amplified bovine LAMAN cDNA from an α-mannosidosis affected Angus calf showing a $T^{961}>C$ transition resulting in $Phe^{321}>Leu$ substitution is shown in (FIG. 9A). Partial sequence of amplified LAMAN cDNA from a Galloway heterozygous for α-mannosidosis showing a partial $G^{662}>A$ transition resulting in $Arg^{221}>His$ substitution is shown in (FIG. 9B).

LAMAN fibroblast cDNA from normal and affected Angus cattle were compared by direct sequencing of PCR products. A single nucleotide transversion, $T^{961}$>C, was discovered that was predicted to result in phe$^{321}$>leu substitution (FIG. 9). Sequence alignment studies with α-mannosidase sequences from other species (eg. yeast, rat, D. disc, cow, human, mouse, pig and Drosophila) have shown that Phe$^{321}$ is conserved within the class 2 α-mannosidase family indicating that it serves an important physiological function. Recently we discovered that the $T^{961}$>C transversion was conserved in both alleles of three affected Angus cattle, in one of the alleles of twelve carriers and in no alleles of fifty-eight normal Angus cattle.

Alpha-mannosidosis among Galloway cattle

The α-mannosidase activity in a liver extract from Alpha-mannosidosis affected Galloway cattle was 1.8% of normal. A similar activity was detected in the liver extract from an affected Angus x Galloway crossbreed. About 90% of these activities were immunoprecipitated indicating that they resulted predominantly from the expression of LAMAN. The temperature stability of LAMAN from affected Galloway cattle was different from the LAMAN stability from normal cattle and affected Angus cattle. LAMAN from affected Galloway was heat denatured in two phases, 80% being denatured with $T_{1/2}$ of 60° C. and 20% denatured with $T_{1/2}$ of 83° C. Both normal LAMAN and LAMAN from affected Angus was heat denatured in one phase with $T_{1/2}$ of 70° C.

Comparison of the sequences of normal LAMAN cDNA and fibroblast cDNA from a carrier of Galloway breed revealed a difference in a single position. A single nucleotide transversion, $G^{662}$>A was discovered that was predicted to result in arg$^{221}$>his substitution. In a Galloway carrier there are two bases in position 662 because of the presence of a normal allele (G662) and a mutated allele (A662) (FIG. 9). In this position only arg or lys appear within the class 2 α-mannosidase family indicating that these closely related side chains are physiologically important at this site. The $G^{662}$>A transition was recently discovered in both alleles of two affected Galloway cattle, in one of the alleles of seven carriers and in no alleles of twenty-nine normal Galloway cattle.

Organisation of the LAMAN gene

The intron-exon boundaries were characterised by sequencing of PCR products from bovine genomic DNA using as primers oligonucleotide sequences from the bovine cDNA or intronic sequences that was determined from the PCR products. The LAMAN gene spanned approximately 16 kb and consisted of 24 exons. Exon 1 encoded the signal peptide and 4 amino acids of peptide a. Exon 24 encoded 36 amino acids at the carboxyterminal end of peptide e. All intron-exon junctions fitted the GT/AG consensus rule (FIG. 10).

Summary

We have purified to homogeneity and characterised lysosomal α-mannosidase (LAMAN) from bovine kidneys. Its cDNA containing the complete open reading frame of 2997 bp was sequenced. The mature enzyme consisted of five different peptides. Four of these peptides were aminoterminally sequenced and found to be identical to internal sequences within the deduced cDNA sequence. The peptide that was not sequenced, the 13/15 kDa peptide was identical in molecular mass to a human LAMAN peptide. The N-terminal amino acid sequence of this human peptide was more than 60% identical to pos. 872–889 of the deduced bovine LAMAN amino acid sequence indicating that position 872 is a potential cleavage site. Such a cleavage would generate a peptide of the expected size of 14 kDa. Thus, bovine, LAMAN was probably synthesized as a one chain precursor that was processed into five peptides.

The amino acid sequence exhibited 83% identity with the deduced amino acid sequence of a putative human retina LAMAN cDNA (Nebes, V. L. and Schmidt, M. C., 1994, Biochem. Biophys. Res. Comm., 200: 239–245) except for regions that in the bovine LAMAN sequence are located in pos. 510–550, 571–588 and 865–898. A comparison with the deduced amino acid sequence of a human placenta LAMAN cDNA revealed a high degree of similarity with the bovine sequence throughout the entire sequence.

To distinguish the peptides within the LAMAN complex we suggest to name them in alphabetic order according to their original position relative to the N-terminus of the one chain precursor. Thus, the 35/38 kDa peptide was named peptide a, the 11/13 kDa peptide was peptide b, the 22 kDa peptide was peptide c, the 38 kDa peptide was peptide d and the 13/15 kDa peptide was peptide e (Table 2). This peptide pattern has never before been reported for any LAMAN.

Prior to reduction there were three peptides of 67 kDa, 38 kDa and 13/15 kDa of which the 67 kDa peptide contained peptide a, peptide b and peptide c joined by disulfide bridges.

In addition to exon 1 that encoded the signal peptide there were 23 exons within a 16 kb region. The exon/intron boundaries were identical to those in human LAMAN but the intron sizes varied. The elucidation of the exon/intron organisation is important for the construction of DNA-based mutation detection systems for bovine Alpha-mannosidosis and for the study of exon/intron organisation of LAMAN in other species.

One of the aims of this study was to determine if the variation of the clinical expressions between alpha-mannosidosis affected cattle of Galloway and Angus breeds could be explained by a different genotype. Affected cattle from both breeds expressed acid α-mannosidase activities that were precipitated by the antersium. This indicated that the mutations did not result in a major disruption of the LAMAN polypeptide chain. Thus, not unexpectedly the mutations G662A and T961C were nucleotide substitutions that resulted in the single amino acid changes R221H and F321L. The mutated enzyme from Angus appeared to be similarly heat stable as normal LAMAN, but more heat stable than the mutated enzyme from Galloway cattle confirming that the disorders in Angus and Galloway were caused by different mutations.

The mutation in Angus apparently resulted in the reduced expression of LAMAN polypeptide, while the temperature stability and specific activity appeared unchanged. It is possible that the mutation caused destabilization of a folding intermediate, resulting in the majority of the precursor being misfolded and prematurely degraded. The mutation in Galloway, however, caused a change of the temperature stability indicating that the conformation of the mature enzyme had been changed. The biphasic temperature denaturation event suggested that the mutated enzyme exists in different conformational isoforms. While the Angus mutation apparently resulted in the substitution of a highly conserved phenylalanine for a leucine within a region containing few conserved amino acids among class 2 α-mannosidases the mutation in Galloway resulted in the substitution of arginine for histidine within a highly conserved region. Possibly, this arginine that is replaced by lysine in ER and yeast α-mannosidases functions close to the active site, and that its substitution results in local conformational changes with high impact on the enzymatic activity. Such a substitution might also alter the substrate specificity with a larger decrease of catalytic activity towards naturally occuring oligosaccharides than against the simple, artificial substrate used in this study. This may explain the apparent 10× higher LAMAN activity in affected Galloway than Angus despite the more severe clinical expression of the disease in Galloway cattle.

The differences of the enzyme properties combined with the variation of the clinical expression between the breeds clearly indicated that molecular heterogeneity exists for α-mannosidosis between the two breeds. The carrier Galloway cow we examined lacked the T961>C transition for which the affected Angus was homozygous. Similarly the affected Angus calf lacked the G662>C transition present in one of the alleles of the Galloway carrier. The T961>C mutation was found in each of 8 affected Angus, in 12 heterozygous but not in 100 Angus classified as non-carriers on the basis of α-mannosidase activity in blood. Similarly the G662>C transition was found on both alleles in 4 affected Galloway calves, 10 putative carriers were heterozygous for this mutation and the mutation was absent from 20 Galloways classified as non-carriers on the basis of enzyme activity in blood. Since these two mutations were the only ones detected by sequencing the complete cDNAs and the corresponding amino acid substitutions involved amino acids that were conserved among class 2 α-mannosidases, we have concluded that they are the disease causing mutations. Interestingly both mutations resulted in the expression of a small, but significant amount of LAMAN-activity. Although it is not known what effect this activity has on the clinical expression its presence in both affected breeds could indicate that some enzyme activity is necessary for the prenatal development. Studies of α-mannosidosis causing mutations in human will indicate whether expression of enzyme activity is common among α-mannosidosis affected individuals. The elucidation of the disease causing mutations in cattle have made possible an improved diagnostic tool for detecting carriers of bovine α-mannosidosis.

EXAMPLE 3

Figure 11:
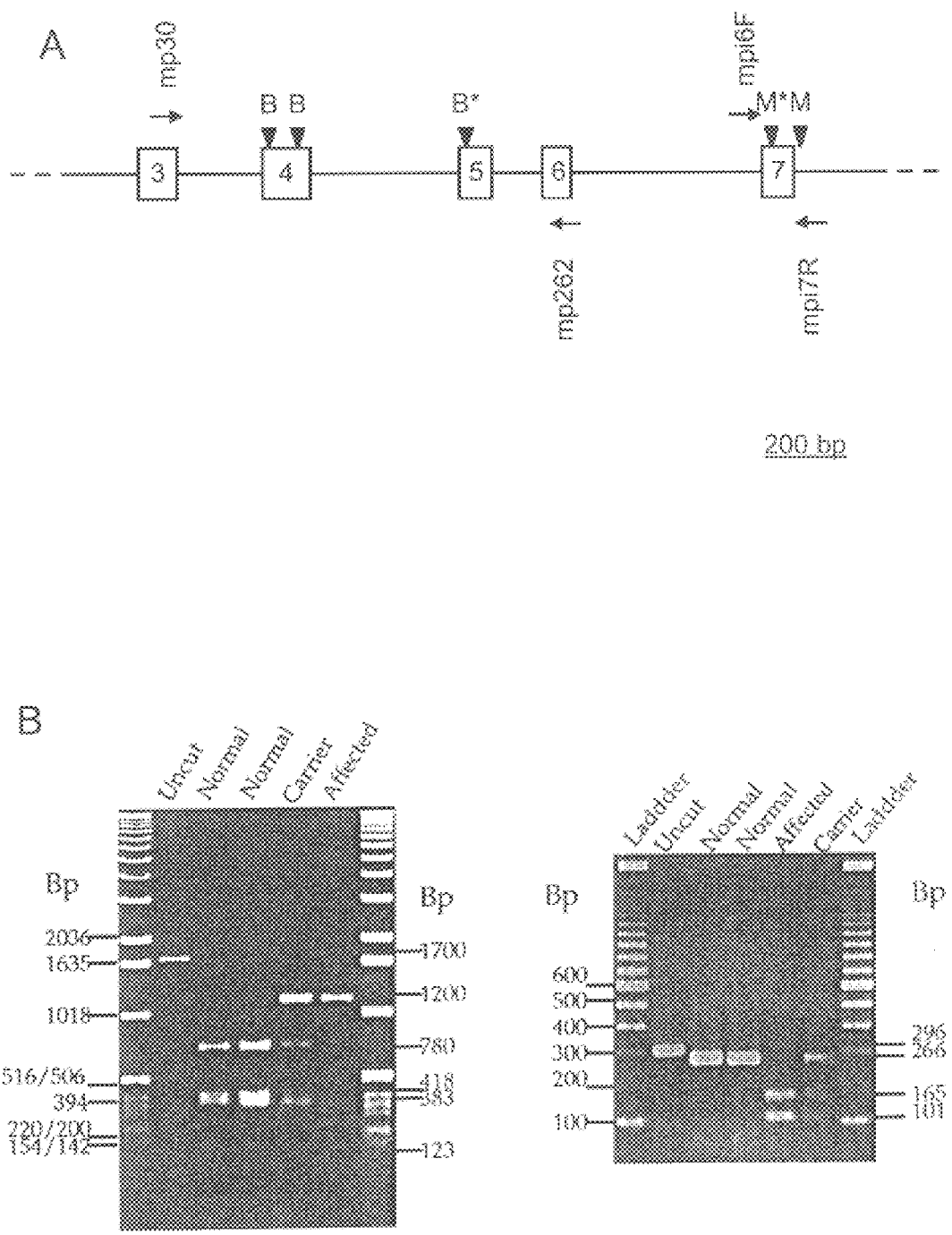
FIG. 11, Part A shows the genomic organisation of LAMAN gene between intron 2 and intron 7. Positions of the primers (mp30, mp262, mpi6F, mpi7R), Mnl I (M) and Bsa HI (B) restriction sites of the two amplicons are indicated. Asterisks indicate the Bsa HI site lost due to the G662A mutation and the Mnl I sites introduced by the T961C mutation.

Screening for the G662A and the T961C mutations by PCR based restriction fragment length polymorphism (RFLP) analysis Methods The G662A and the T961C mutations are in exons 5 and 7 of the LAMAN gene, (FIG. 11A). To Screen for the G662A mutation, a 1700 bp fragment including exon 5 was amplified by PCR in 100 μl containing 100 ng of genomic DNA, 20 pmol of each primer mp262 (5'-GGGCTGCGCGTGTCCTCCACAA-3') (SEQ ID No.8) and mp30 (5'-CAGAAAATCGTGAGGGAACTGGTG-3) (SEQ ID No.9), 100 μM dNTP's, 2U Taq DNA polymerase (Gibco-BRL), 1×PCR buffer (50 mM KCl, 10 mM Tris-HCl, pH 8.3) and 2 mM of $Mg^{2+}$. The reaction was cycled 34 times as follows: 66° C. for 3 minutes and 94° C. for 1 minute. Initial denaturation was 95° C. for 5 minutes and final extension was 7 minutes at 72° C. Twenty μl of the PCR products were digested in the PCR buffer overnight at 37° C. by 2U of Bsa HI.

The T961C mutation was detected by PCR amplification using the primer combination mpi6F (5'-CGCAGGACACCCTAGCCTTAG-3') (SEQ ID No. 7) and mpi7R (5'CCTTGCTATTGTTTTAAGCCTCTAAGTTTG TGGT-3') (SEQ ID No.6).

PCR conditions were as above. The resulting 290 bp PCR products included exon 7 and were digested in the PCR buffer overnight by 2U Mnl I. A Mnl restriction site were introduced to the primer mpi7R to serve as a positive control for digestion. The digests were separated on a 2% agarose gel and visualized by EtBr staining (FIG. 11B).

Results

The G662A mutation removes a Bsa HI restriction site while the T961C mutation introduces a Mnl I site. Hence, both mutations are easily detected by PCR based RFLP on DNA extracted from blood. The tests were also found to work on DNA from semen and hair roots. The assays were used to screen for the mutations in animals whose α-mannosidosis genotype previously had been determined by measuring the LAMAN activity by the granulocyte or plasma test. The affected Angus cattle were homozygous, and all carrier Angus, Red Angus and Murray Grey cattle were heterozygous for the T961C mutation. No normal animals carried the T961C mutation. The animals were from unrelated herds from different parts of Australia, except for 7 Red Angus of which 4 were carriers of T961C, providing evidence that the T961C mutation is present in North American Angus breeds. All affected Galloways were homozygous, and the carrier Galloways were heterozygous for the G662A mutation. No normal animals carried the G662A mutation.

What is claimed is:

1. A method for diagnosing or screening for bovine α-mannosidosis, comprising detecting, in nucleic acid samples from cattle, the presence or absence of an α-mannosidosis causing mutation in a nucleic acid encoding bovine lysosomal α-mannosidosis (LAMAN), wherein said mutation is a T to C transition at position 975 of SEQ ID NO: 1 or is a G to A transition at position 677 of SEQ ID NO: 1, and wherein the presence of the mutation is indicative of a diseased or carrier animal, thereby diagnosing or screening for bovine α-mannosidosis.

2. A method of detecting α-mannosidosis-causing mutations in cattle, comprising detecting, in nucleic acid samples from cattle, the presence or absence of a base transition in a nucleic acid encoding bovine LAMAN, wherein said transition is an α-mannosidosis-causing mutation, and wherein said transition is a T to C transition at position 975 of SEQ ID NO: 1 or is a G to A transition at position 677 of SEQ ID NO: 1, thereby detecting α-mannosidosis-causing mutations in cattle.

3. A method as claimed in claim 1 wherein the α-mannosidosis causing mutation is said T to C transition.

4. A method as claimed in claim 1 wherein the α-mannosidosis causing mutation is said G to A transition.

5. A method as claimed in claim 1, 2 or 3, wherein the cattle are of the Angus or Angus-derived breed.

6. A method as claimed in claim 1, 2 or 4, wherein the cattle are of the Galloway breed.

7. A method as claimed in claim 1, wherein the nucleic acid sample is amplified prior to detection of the mutation.

8. A method as claimed in claim 1, wherein the method of detecting comprises a step of digesting the nucleic acid samples with a restriction enzyme.

9. A method as claimed in claim 8, wherein the mutation is detected by restriction fragment length polymorphism (RFLP) analysis.

10. A method as claimed in claim 8 or 9, wherein the restriction enzyme is Mnl T.

11. A method as claimed in claim 8 or 9, wherein the restriction enzyme is Bsa HI.

12. A method as claimed in claim 1, wherein the nucleic acid samples are DNA samples.

13. A method as claimed in claim 1, wherein the nucleic acid samples are from the roots of hair taken from the cattle.

14. An oligonucleotide primer selected from the group consisting of SEQ ID NOS. 5 to 10 for use in the detection of α-mannosidosis causing mutations.

15. An oligonucleotide primer selected from the group consisting of SEQ ID NOS. 5 to 10 for use in amplification of nucleic acid prior to detection of an α-mannosidosis-causing mutation.

16. An isolated nucleic acid fragment encoding a mutated bovine LAMAN protein, wherein said nucleic acid fragment comprises the bovine LAMAN open reading frame of nucleotides 15 to 3085 of SEQ ID NO: 1, with the exception that the open reading frame has a T to C transition at position 975 of SEQ ID NO: 1 or a G to A transition at position 677 of SEQ ID NO: 1.

* * * * *